United States Patent [19]
Hirate et al.

[11] Patent Number: 5,643,795
[45] Date of Patent: Jul. 1, 1997

[54] APPARATUS FOR PURIFYING CONTAMINATED AIR

[75] Inventors: Ken Hirate, Sagamihara; Kazumi Kaneko; Shinichiro Sato, both of Yokohama; Kazunori Watagami, Nagoya, all of Japan

[73] Assignee: Fujita Corporation, Tokyo, Japan

[21] Appl. No.: 411,568

[22] Filed: Mar. 28, 1995

[51] Int. Cl.$^6$ ................................ C12M 1/16; C12S 5/00
[52] U.S. Cl. .................. 435/299.1; 435/266; 435/289.1; 404/71; 55/385.1
[58] Field of Search ................ 435/266, 262.5, 435/286.6, 289.1, 290.1, 299.1; 422/122, 120; 55/385.1, 385.2, DIG. 30; 404/1, 2, 4, 25, 71; 4/219; 454/48, 166, 167, 237, 251, 902

[56] References Cited

U.S. PATENT DOCUMENTS

| | | | |
|---|---|---|---|
| 3,385,196 | 5/1968 | Messen-Jaschin | 55/385.1 |
| 3,434,267 | 3/1969 | Messen-Jaschin | 55/385.1 |
| 3,747,502 | 7/1973 | Williams | 404/4 |
| 4,961,763 | 10/1990 | Thompson et al. | 55/312 |
| 4,975,251 | 12/1990 | Saceman | 422/124 |

FOREIGN PATENT DOCUMENTS

| | | | |
|---|---|---|---|
| 2721048 | 11/1978 | Germany | 435/266 |
| 5-98829A | 4/1993 | Japan | E04H 6/08 |
| 5-103947A | 4/1993 | Japan | B01D 53/34 |
| 5-137947A | 6/1993 | Japan | B01D 53/34 |
| 5-329323A | 12/1993 | Japan | B01D 53/34 |
| 5-315607 | 11/1994 | Japan | 422/122 |
| 5-315608 | 11/1994 | Japan | 422/122 |
| 679644 | 3/1992 | Switzerland | 435/266 |
| 2254764 | 10/1992 | United Kingdom . | |
| 93/02716A1 | 2/1993 | WIPO . | |

OTHER PUBLICATIONS

WPI Abstract No. 93-211437/26 JP 05137947 (1995).

Primary Examiner—William H. Beisner
Attorney, Agent, or Firm—Ronald R. Snider

[57] ABSTRACT

An apparatus for purifying contaminated air has an air inlet exposed to a road surface, an air outlet spaced from the road surface, a soil bed for being populated with microorganisms, the soil bed being disposed between the air inlet and the air outlet and allowing air to pass therethrough, a pipe interconnecting the soil bed and the air outlet, and embedded underground, and a fan for introducing air from the air inlet, passing the air through the soil bed, delivering the air from the soil bed through the pipe to the air outlet, and discharging the air from the air outlet.

2 Claims, 17 Drawing Sheets 5,643,795

APPARATUS FOR PURIFYING CONTAMINATED AIR

BACKGROUND OF THE INVENTION

1. Field of the Invention

The present invention relates to an apparatus for purifying contaminated air in the environmental atmosphere.

2. Description of the Related Art

There has been known a conventional method of purifying contaminated air in the environmental atmosphere by passing the contaminated air through a soil layer populated with microorganisms to allow the contaminants in the contaminated air to be degraded by the microorganisms in the soil layer. Such a purifying method and an apparatus for carrying out the method have proven much more satisfactory than traditional methods of and apparatus for purifying contaminated air. However, while a wide variety of potential applications may possibly be available for the existing method and apparatus, only some of them have been proposed so far in the art.

SUMMARY OF THE INVENTION

It is an object of the present invention to provide an apparatus for purifying contaminated air in the environmental atmosphere by passing the contaminated air through a soil layer populated with microorganisms to allow the contaminants in the contaminated air to be degraded by the microorganisms in the soil layer, the apparatus being improved so as to be applicable to a variety of new applications.

According to the present invention, there is provided an apparatus for purifying contaminated air, comprising an air inlet exposed to a road surface, an air outlet spaced from the road surface, a soil bed for being populated with microorganisms, the soil bed being disposed between the air inlet and the air outlet and allowing air to pass therethrough, a pipe interconnecting the soil bed and the air outlet, and embedded underground, and air flowing means for introducing air from the air inlet, passing the air through the soil bed, delivering the air from the soil bed through the pipe to the air outlet, and discharging the air from the air outlet.

According to the present invention, there is also provided an apparatus for purifying contaminated air, comprising a three-dimensional structure including a ground level and an artificial foundation disposed above the ground level with a space defined between the ground level and the artificial foundation, a planted zone including a soil bed disposed on the artificial foundation for being populated with microorganisms, the soil bed allowing air to pass vertically therethrough, and plants cultivated on the soil bed, an air passage communicating between the space and a bottom of the soil bed, and a fan disposed in the air passage for flowing air from the space through the air passage to the bottom of the soil bed.

According to the present invention, there is further provided an apparatus for purifying contaminated air, comprising a soil bed for being populated with microorganisms, the soil bed allowing air to pass vertically therethrough and having plants cultivated thereon, a container having side walls and a bottom wall joined thereto, the container accommodating the soil bed, a case connected to the container, the case having an air inlet, an air passage connected to a bottom of the soil bed, and a fan housed in the case for introducing air from the air inlet and supplying the air to the air passage.

According to the present invention, there is also provided an apparatus for purifying contaminated air, comprising a case, a soil bed accommodated in the case for being populated with microorganisms, the soil bed allowing air to pass therethrough, an air outlet embedded in the soil bed, a pipe interconnecting the air outlet and an exterior space around the case, and a fan connected to the pipe for flowing air from the exterior space through the pipe into the air outlet and then through the soil bed back into the exterior space, the case having an open top wall and an air-permeable bottom wall for allowing air to pass therethrough.

According to the present invention, there is further provided an apparatus for purifying contaminated air, comprising a case, a soil bed accommodated in the case for being populated with microorganisms, the soil bed allowing air to pass therethrough, an air outlet embedded in the soil bed, a pipe interconnecting the air outlet and an exterior space around the case, and a fan connected to the pipe for flowing air from the exterior space through the pipe into the air outlet and then through the soil bed back into the exterior space, the case having at least two opposite air-permeable side walls for allowing air to pass therethrough.

According to the present invention, there is still further provided an apparatus for purifying contaminated air, comprising a case, a soil bed accommodated in the case for being populated with microorganisms, the soil bed allowing air to pass therethrough, an air inlet embedded in the soil bed, a pipe interconnecting the air inlet and an exterior space around the case, and a fan connected to the pipe for flowing air from the exterior space through the air inlet, the soil bed, and the pipe back into the exterior space, the case having an open top wall and an air-permeable bottom wall for allowing air to pass therethrough.

The above and other objects, features, and advantages of the present invention will become apparent from the following description when taken in conjunction with the accompanying drawings which illustrate preferred embodiments of the present invention by way of example.

DETAILED DESCRIPTION OF THE PREFERRED EMBODIMENTS

Figure 1:
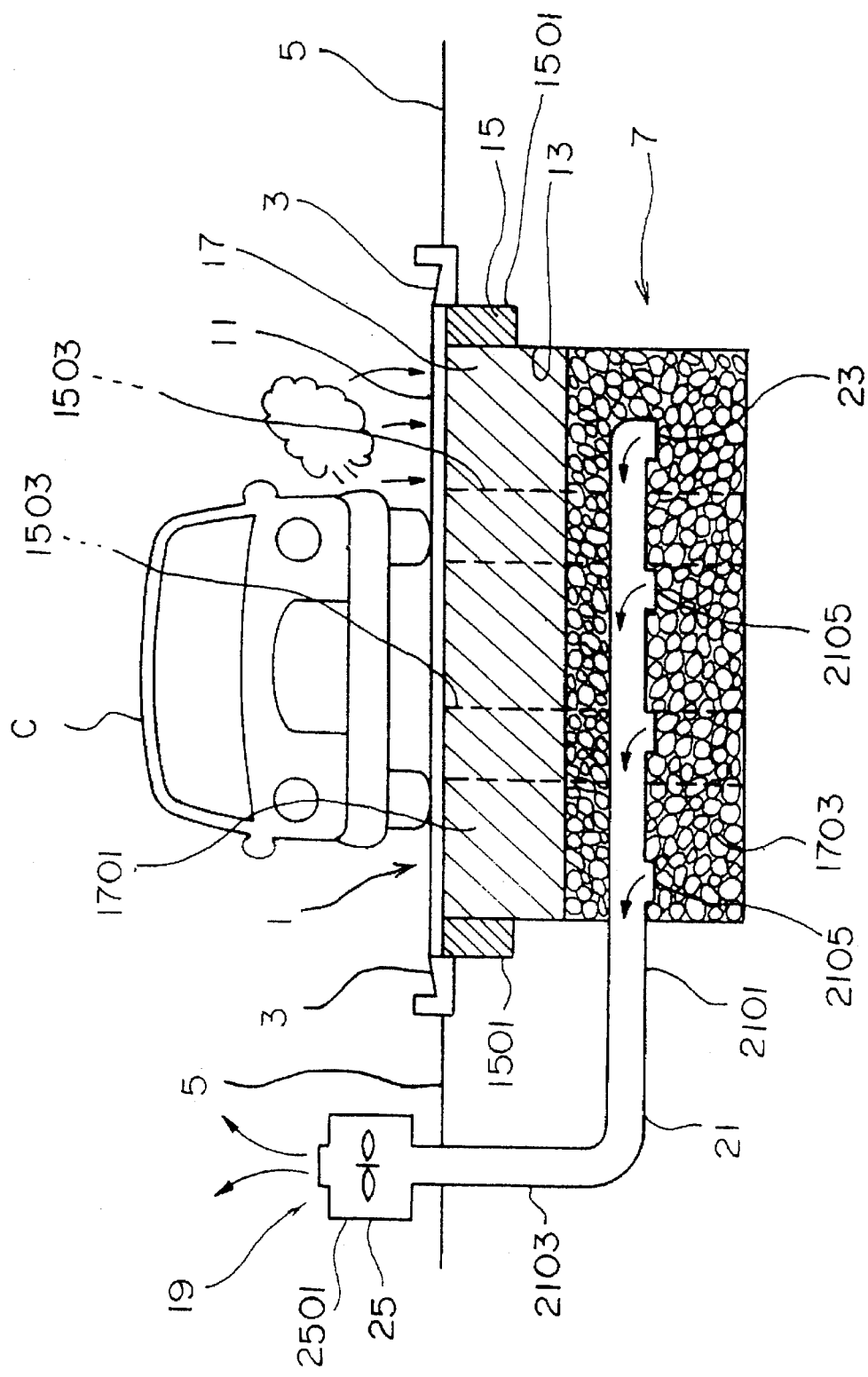
FIG. 1 is a vertical cross-sectional view of a contaminated air purifying apparatus according to a first embodiment of the present invention.
Figure 2:
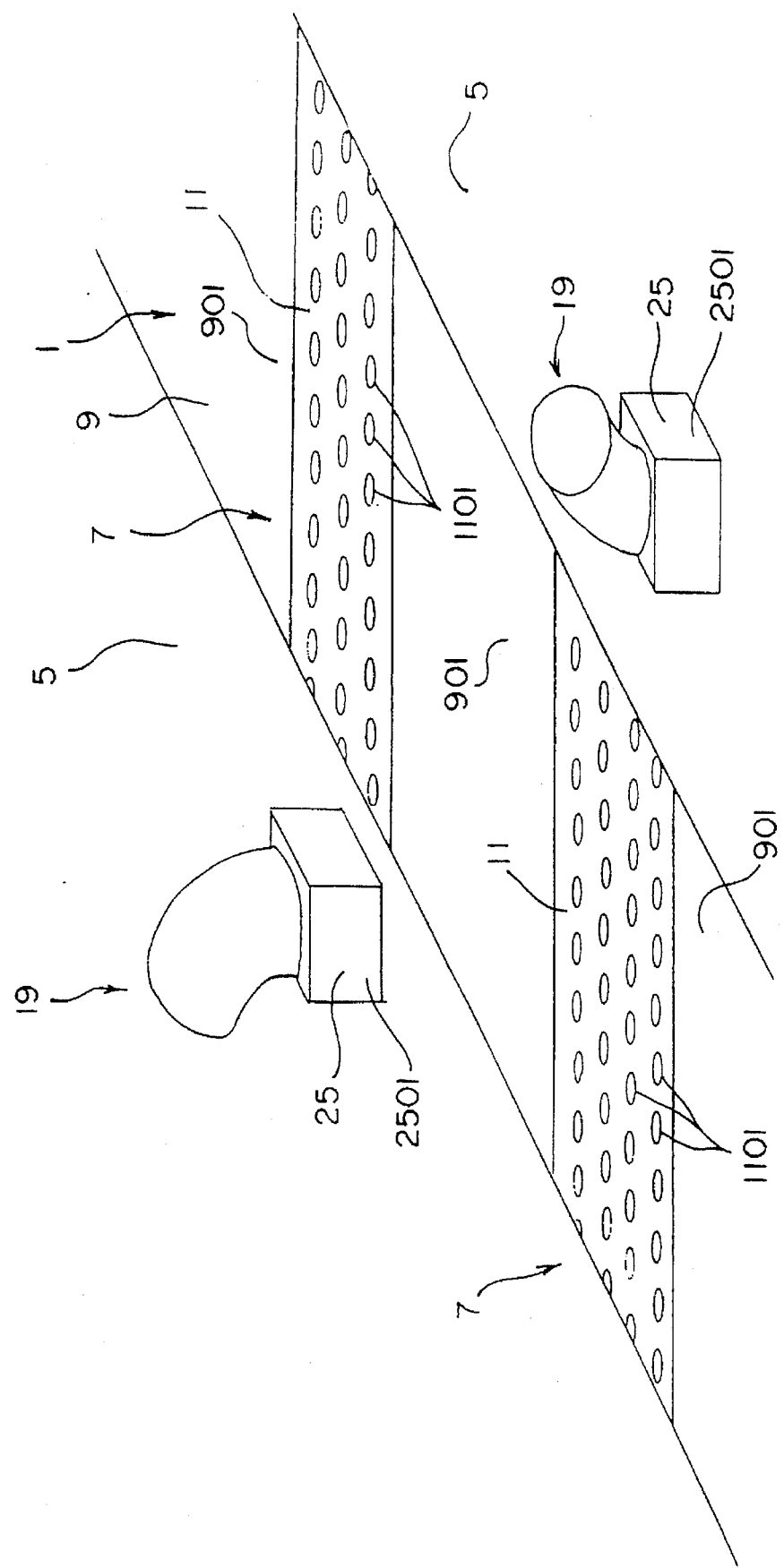
FIG. 2 is a perspective view of an overground portion of the contaminated air purifying apparatus according to the first embodiment of the present invention.

As shown in FIGS. 1 and 2, a contaminated air purifying apparatus 7 according to a first embodiment of the present invention is combined with a road 1, a pair of side gutters 3 positioned one on each side of the road 1, and a pair of sidewalks 5 extending outwardly of the side gutters 3. The contaminated air purifying apparatus 7 comprises an apertured plate 11 serving as a surface 9 of the road 1, a hole 13 defined in the road 1 below the apertured plate 11, a support 15 which supports the apertured plate 11 at a predetermined height, a soil bed 17 accommodated in the hole 13, an air outlet port 19 positioned on one of the sidewalks 5, a pipe 21 extending underground between the soil bed 17 and the air outlet port 19, an air inlet 23 on the pipe 21, and a fan 25 connected to the pipe 21 at the air outlet port 19. A plurality of such contaminated air purifying apparatus 7 are positioned at spaced intervals along the road 1.

The apertured plate 11 is made of a material having a high mechanical strength such as precast concrete, and extends between the side gutters 3. The apertured plate 11 has a number of apertures 1101 defined therein.

The hole 13 defined in the road 1 is of a shape complementary to the apertured plate 11 so that the apertured plate 11 is snugly fitted in the upper opening of the hole 13.

The support 15 serves to support the apertured plate 11 at the same height as an adjacent road surface 901 of the road 1. The support 15 comprises a pair of foundations 1501 placed in the road 1 near the respective side gutters 3, and a plurality of vertical posts 1503 positioned in the hole 13 at a longitudinally intermediate region of the apertured plate 11 and having lower ends driven into the bottom of the hole 13. When an automobile C is positioned on the apertured plate 11, the weight of the automobile C is borne by the foundations 1501 and the posts 1503.

The soil bed 17 accommodated in the hole 13 is composed of a soil layer 1701 and a broken stone layer 1703 disposed underneath the soil layer 1701. The soil layer 1701 comprises a layer of soil for populating microorganisms therein, e.g., a layer of andosols, so that air can flow vertically through the soil layer 1701. The broken stone layer 1703 comprises a number of broken or crushed stones. Rainwater that has been introduced from the apertured plate 11 into the soil bed 17 flows successively through the soil layer 1701 and the broken stone layer 1703, and then permeates the ground therebelow.

The pipe 21 extends substantially perpendicularly to the longitudinal direction of the road 1, and comprises a horizontal section 2101 embedded in the broken stone layer 1703 substantially the entire width of the road surface 9, and a vertical section 2103 extending upwardly from one end of the horizontal section 2101 below one of the sidewalks 5 outside of the broken stone layer 1703. The vertical section 2103 has an upper end portion projecting above the sidewalk 5 and connected to the fan 25 which has a fan case 2501. The air outlet port 19 is defined in the fan case 2501.

The horizontal section 2101 has a plurality of suction pipes 2105 spaced at intervals therealong and projecting downwardly. The suction pipes 2105 correspond to the air inlet 23.

Operation of the contaminated air purifying apparatus 7 will be described below.

A power supply (not shown) is connected to rotate the fan 25. When the fan 25 is rotated, air in the broken stone layer 1703 is drawn through the suction pipes 2105 into the horizontal section 2101 and then the vertical section 2103, from which it is discharged through the air outlet port 19.

When the air is drawn from the broken stone layer 1703, contaminated air is introduced through the apertures of the apertured plate 11 into the soil bed 17 from its upper surface, and flows through the soil layer 1701 toward the broken stone layer 1703.

When the contaminated air is flowing through the soil layer 1701, the soil layer 1701 performs a physical action as a filter to trap dust particles and adsorbs impurities such as a hydrocarbon gas such as methane or the like.

The microorganisms contained in the soil layer 1701 degrade or decompose those impurities or noxious gases.

Specifically, aerobic microorganisms are populated on the surface of the soil bed 17 and in regions of the soil bed 17 where air flows, and anaerobic microorganisms are populated in regions of the soil bed 17 where no air flows. When the contaminated air is consumed or inhaled by the microorganisms, the microorganisms chemically transform or degrade various contaminant gases in the contaminated air, e.g., carbon monoxide into carbon dioxide, nitrogen monoxide into nitrate ions, and methane into carbon dioxide and water. In this manner, various contaminants contained in the contaminated air are removed by the soil bed 17.

Clean air from which the contaminants have been removed is then discharged from the air outlet port 17 over the sidewalk 5.

In this embodiment, the contaminated air purifying apparatus 7 is incorporated in a portion of the road surface 9 and a region below the portion of the road surface 9, and draws in contaminated air from above the road surface 9 and discharges clean air over the sidewalk 5.

Since only the air outlet port 19 is installed on the sidewalk 5, no large facility space is required on the sidewalk 5 and the appearance of the sidewalk 5 is not essentially impaired. In addition, the contaminated air purifying apparatus 7 can discharge clean air over the sidewalk 5 in the vicinity of a road region where a traffic jam is likely to occur.

An experiment was conducted on the contaminated air purifying apparatus 7 as follows:

The apertures 1101 of the apertured plate 11 had a diameter of about 20 mm. The soil layer 1701 had a thickness of about 50 cm, and the broken stone layer 1073 was composed of broken stones having a diameter of about 5 cm and had a thickness of about 60 cm.

The soil layer 1701 was composed of soil mixed with perlite and vermiculite for higher air and water permeability, and also with peat moss, leaf mold, and compost for a higher content of organic substances.

The pipe 21 had a diameter of about 300 mm.

The fan 25 had an air displacement capability of 54 $cm^3/hr$.

The average concentrations of NOx and CO in the vicinity of the apertured plate 11 ware 0.35 ppm and 12.0 ppm, respectively, and the average concentrations of NOx and CO in the vicinity of the air outlet port 19 were 0.02 ppm and 0.58 ppm, respectively. Therefore, the removal ratio for NOx was 94%, and the removal ratio for CO was 95%.

Figure 3:
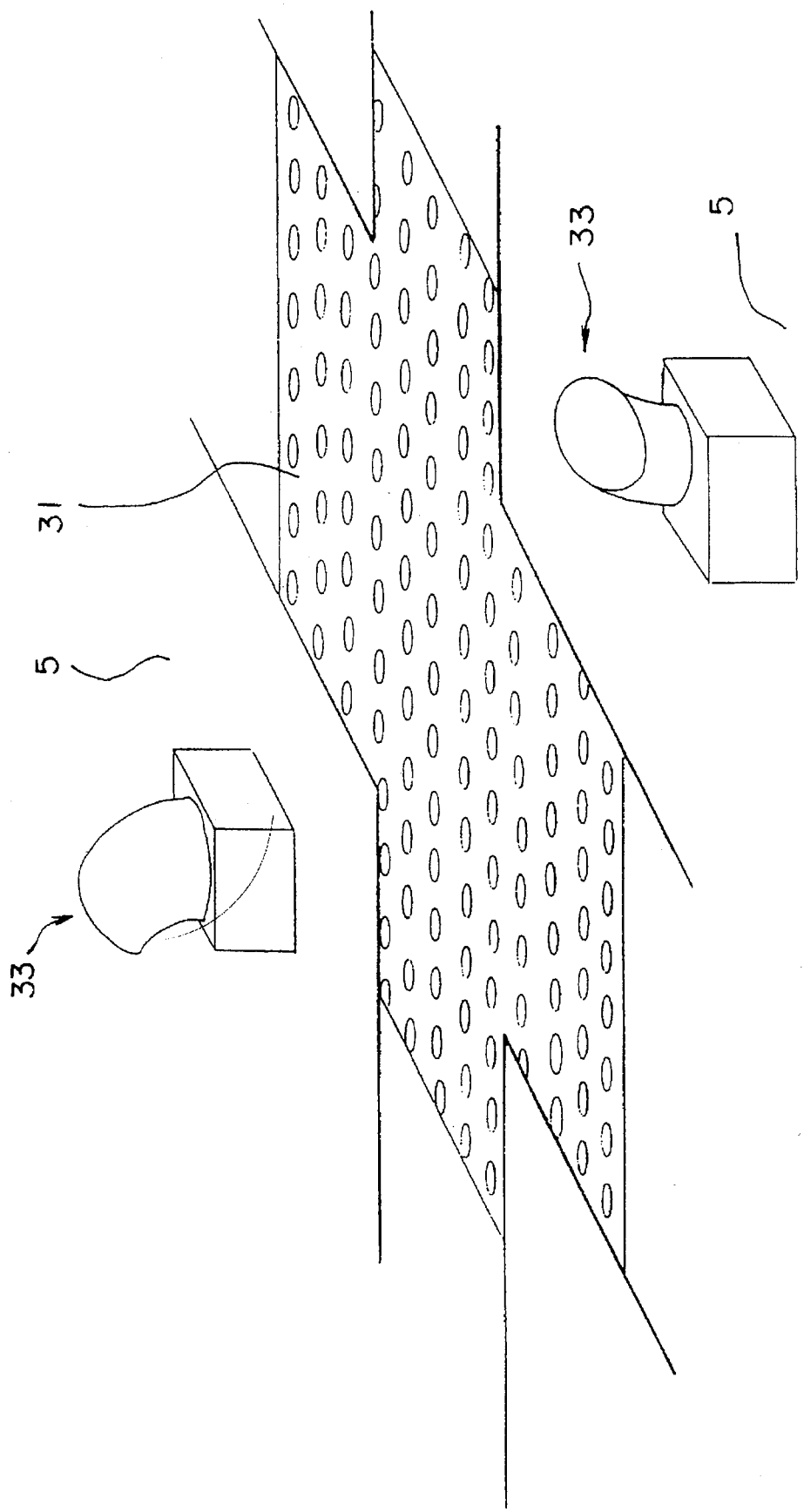
FIG. 3 is a perspective view of an overground portion of a modified contaminated air purifying apparatus which is incorporated in an intersection.

FIG. 3 shows in perspective an overground portion of a modified contaminated air purifying apparatus which is incorporated in an intersection.

As shown in FIG. 3, the modified contaminated air purifying apparatus has an apertured plate 31 of a crisscross shape fitted in an intersection, and two air outlet ports 33 disposed on two diagonal corners of sidewalks 5. Below the apertured plate 31, there are disposed a hole, a soil bed, a support, and a pipe which are identical to those of the contaminated air purifying apparatus 7 according to the first embodiment shown in FIG. 1.

In the first embodiment shown in FIG. 1, the soil bed 17 includes the broken stone layer 1703 in its lower portion and clean air is drawn in from the broken stone layer 1703. However, an apertured plate may be placed on the bottom of the soil layer 1701 to define a space below the soil layer 1701, and clean air may be drawn in from the space.

The apertures 1101 may be of any of various desired shapes, and the air outlet port 19 may be of any of various desired structures and may be positioned anywhere as desired.

A contaminated air purifying apparatus according to a second embodiment of the present invention, which is incorporated in a road region where a traffic jam tends to happen, will be described below.

Figure 4:
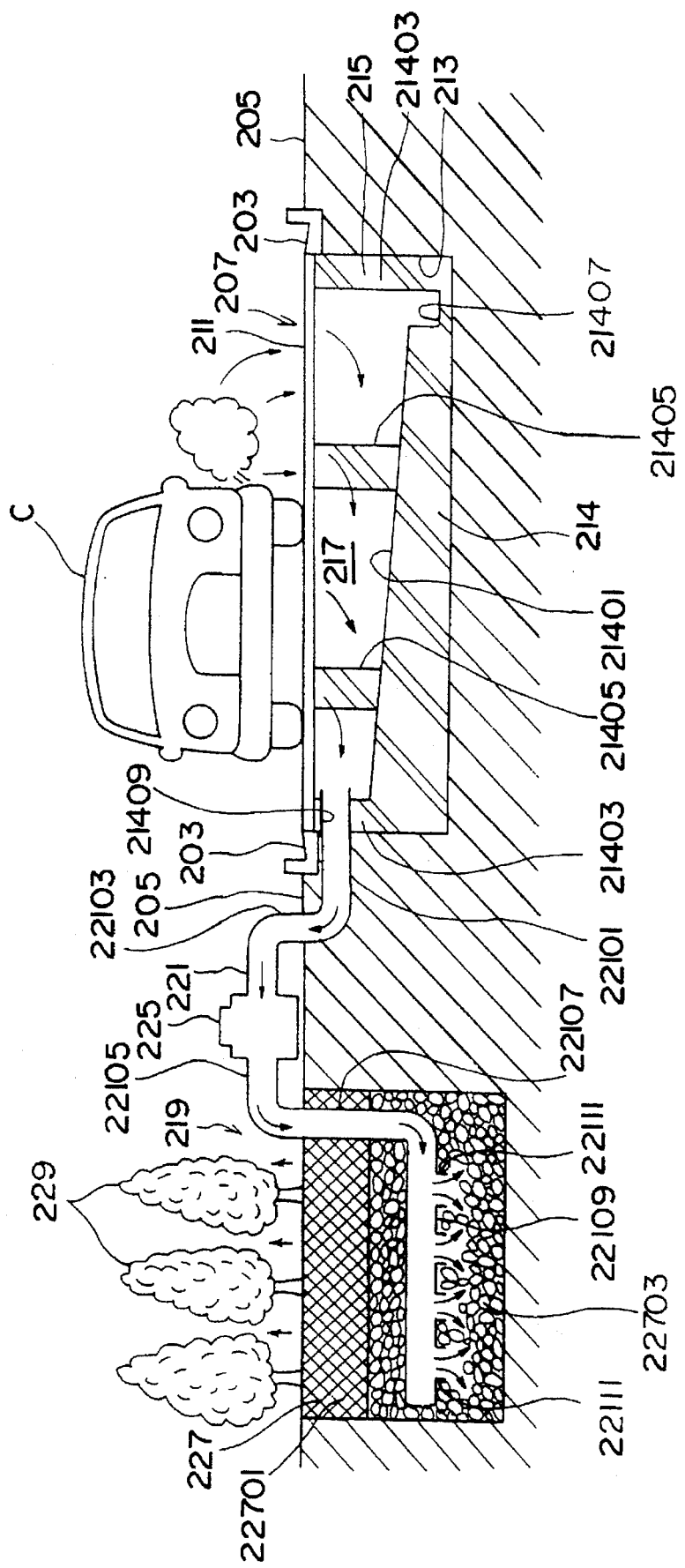
FIG. 4 is a vertical cross-sectional view of a contaminated air purifying apparatus according to a second embodiment of the present invention.
Figure 5:
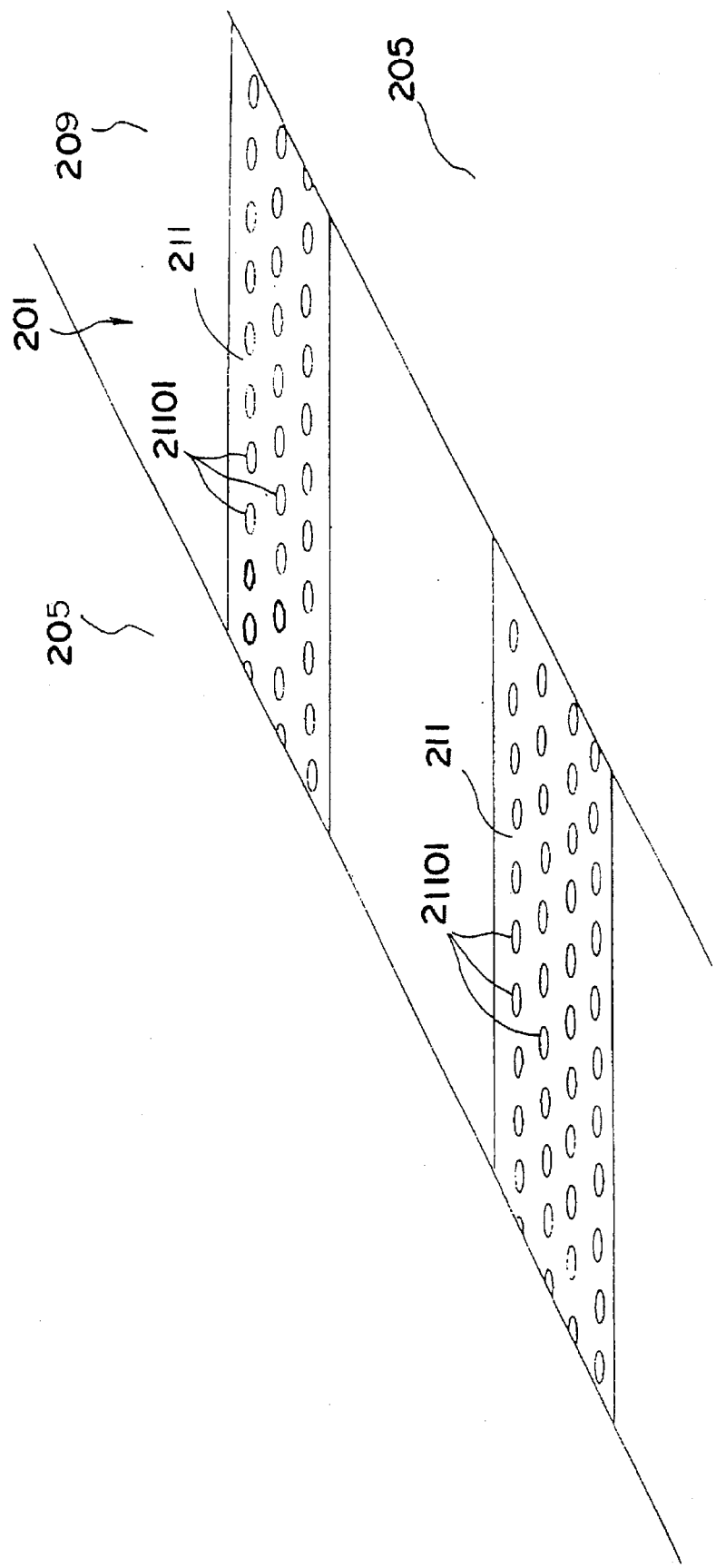
FIG. 5 is a perspective view of an overground portion of the contaminated air purifying apparatus according to the second embodiment of the present invention.

FIG. 4 shows in cross section the contaminated air purifying apparatus, generally denoted at 207, according to the second embodiment of the present invention, and FIG. 5 shows in perspective an overground portion of the contaminated air purifying apparatus according to the second embodiment of the present invention.

As shown in FIGS. 4 and 5, the contaminated air purifying apparatus 207 according to the second embodiment of the present invention is combined with a road 201, a pair of side gutters 203 positioned one on each side of the road 201, and a pair of sidewalks 205 extending outwardly of the side gutters 203. The contaminated air purifying apparatus 207 comprises an apertured plate 211 serving as a surface 209 of the road 201, a hole 213 defined in the road 201 below the apertured plate 211, a support 215 which supports the apertured plate 211 at a predetermined height, a space or chamber 217 defined in the hole 213 below the apertured plate 211, a planted zone 219 positioned adjacent to one of the sidewalks 205 and extending along the road 201, a pipe 221 interconnecting the space 217 and a bottom region of the planted zone 219, and a fan 225 disposed in the pipe 221. A plurality of such contaminated air purifying apparatus 207 are positioned at spaced intervals along the road 201.

The apertured plate 211 is made of a material having a high mechanical strength such as precast concrete, and extends between the side gutters 203. The apertured plate 211 has a number of apertures 21101 defined therein.

The hole 213 defined in the road 201 is of a shape complementary to the apertured plate 211 so that the apertured plate 211 is snugly fitted in the upper opening of the hole 213. A concrete body 214 is disposed on the bottom of the hole 213.

The concrete body 214 may be formed by casting concrete at the site, or may be formed at a factory and then delivered to the site for installation.

The concrete body 214 has a bottom panel including an upper slanted surface 21401, a pair of side walls 21403 projecting upwardly from opposite sides of the bottom panel and positioned one on each side of the road 201, a plurality of posts 21405 projecting upwardly from the upper slanted surface 21401, and a drain gutter 21407 defined in the upper slanted surface 21401.

The upper slanted surface 21401 is inclined upwardly toward the sidewalk 205 which is associated with the planted zone 219. The drain gutter 21407 is defined in a lower side of the upper slanted surface 21401. The side wall 21403 which is positioned on the higher side of the upper slanted surface 21401 has an opening 21409 defined laterally therethrough.

The side walls 21403 and the posts 21405 jointly serve as the support 215. When an automobile C is positioned on the apertured plate 211, the weight of the automobile C is borne by the side walls 21403 and the posts 21405.

The planted zone 219 which is positioned adjacent to one of the sidewalks 205 and extends along the road 201 is composed of a soil bed 227 and plants 229 cultivated on the soil bed 227.

The soil bed 227 is composed of a soil layer 22701 and a broken stone layer 22703 disposed underneath the soil layer 22701. The soil layer 22701 comprises a layer of soil for populating microorganisms therein, e.g., a layer of andosols, so that air can flow vertically through the soil layer 22701. The broken stone layer 22703 comprises a number of broken or crushed stones. Rainwater that has fallen onto the planted zone 219 flows successively through the soil layer 22701 and the broken stone layer 22703, and then permeates the ground therebelow.

The pipe 221 extends substantially perpendicularly to the longitudinal direction of the road 201, and comprises a first horizontal section 22101 embedded in the sidewalk 205 and connected to the opening 21409, a first vertical section 22103 extending upwardly from an end of the first horizontal section 22101 and exposed over the sidewalk 205, a second horizontal section 22105 extending horizontally from an end of the first vertical section 22103 toward the planted zone 219, a second vertical section 22107 extending downwardly from an end of the second horizontal section 22105 into the soil bed 227, a third horizontal section 22109 extending horizontally from an end of the second vertical section 22107 in the broken stone layer 22703, and a plurality of air outlet pipes 22111 projecting downwardly from a lower surface of the third horizontal section 22109. The fan 225 is disposed in the second horizontal section 22105.

Operation of the contaminated air purifying apparatus 207 will be described below.

A power supply (not shown) is connected to rotate the fan 225. When the fan 225 is rotated, air in the space 217 is drawn through the opening 21409 into the pipe 221, and introduced from the air outlet pipes 22111 into the broken stone layer 22703.

Contaminated air over the apertured plate 211 is drawn through the apertures 21101 and the pipe 221 into the broken stone layer 22703, and then discharged upwardly through the broken stone layer 22703 and the soil layer 22701 into the atmosphere.

When the contaminated air is flowing through the soil layer 22701, the soil layer 22701 performs a physical action as a filter to trap dust particles and adsorbs impurities such as a hydrocarbon gas such as methane or the like.

The microorganisms contained in the soil layer 22701 degrade or decompose those impurities or noxious gases.

Specifically, aerobic microorganisms are populated on the surface of the soil bed 227 and in regions of the soil bed 227 where air flows, and anaerobic microorganisms are populated in regions of the soil bed 227 where no air flows. When the contaminated air is consumed or inhaled by the microorganisms, the microorganisms chemically transform or degrade various contaminant gases in the contaminated air, e.g., carbon monoxide into carbon dioxide, nitrogen monoxide into nitrate ions, and methane into carbon dioxide and water. In this manner, various contaminants contained in the contaminated air are removed by the soil bed 17.

Clean air from which the contaminants have been removed is then discharged from the planted zone 219.

In the second embodiment, the contaminated air purifying apparatus 207 is incorporated in a portion of the road surface 209 and the planted zone 219, and draws in contaminated air from above the road surface 209 and discharges clean air over the sidewalk 205.

Since only the fan 225 and a portion of the pipe 221 are installed on the sidewalk 205, no large facility space is required on the sidewalk 205 and the appearance of the sidewalk 205 is not essentially impaired. In addition, the contaminated air purifying apparatus 207 can discharge clean air over the sidewalk 205 in the vicinity of a road region which tends to suffer from a traffic jam.

Even when rainwater is introduced through the apertured plate 211 into the space 217, it flows down the slanted surface 21401 into the drain gutter 21407 and hence is discharged out of the space 217 from the drain gutter 21407. Therefore, no rainwater tends to be trapped below the apertured plate 211.

An experiment was conducted on the contaminated air purifying apparatus 207 as follows:

The apertures 21101 of the apertured plate 211 had a diameter of about 20 mm. The soil layer 22701 had a thickness of about 50 cm, and the broken stone layer 22073 was composed of broken stones having a diameter of about 5 cm and had a thickness of about 60 cm.

The soil layer 22701 was composed of soil mixed with perlite and vermiculite for higher air and water permeability, and also with peat moss, leaf mold, and compost for a higher content of organic substances.

The pipe 221 had a diameter of about 300 mm.

The fan 225 had an air displacement capability of 54 $cm^3/hr$.

The average concentrations of NOx and CO in the vicinity of the apertured plate 211 ware 0.35 ppm and 12.0 ppm, respectively, and the average concentrations of NOx and CO in the vicinity of the planted zone 219 were 0.02 ppm and 0.58 ppm, respectively. Therefore, the removal ratio for NOx was 94%, and the removal ratio for CO was 95%.

Figure 6:
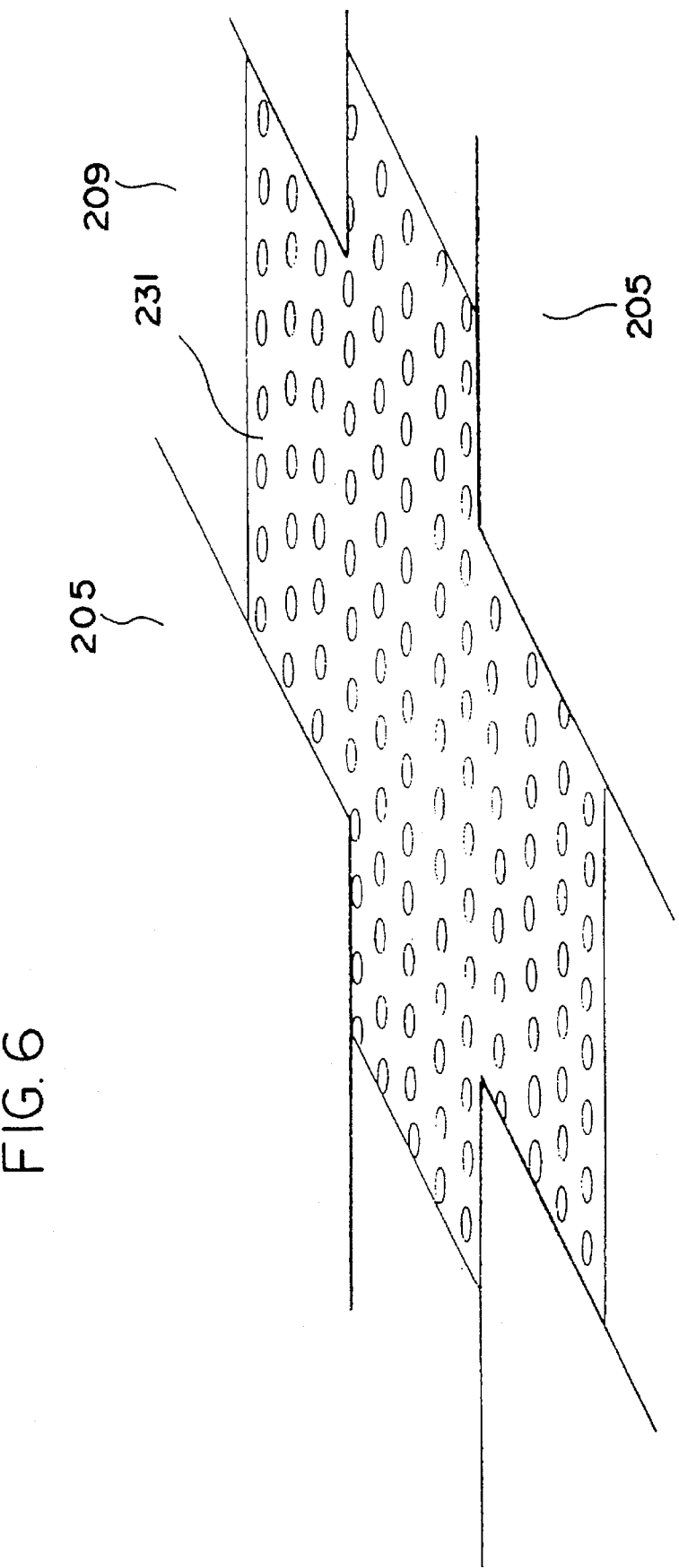
FIG. 6 is a perspective view of an overground portion of a modified contaminated air purifying apparatus.

FIG. 6 shows in perspective an overground portion of a modified contaminated air purifying apparatus which is incorporated in an intersection.

As shown in FIG. 6, the modified contaminated air purifying apparatus has an apertured plate 231 of a criss-cross shape fitted in an intersection. Below the apertured plate 231, there are disposed a hole, a soil bed, a support, and a pipe which are identical to those of the contaminated air purifying apparatus 207 according to the second embodiment shown in FIG. 4.

In the second embodiment shown in FIG. 4, the soil bed 227 includes the broken stone layer 22703 in its lower portion and contaminated air is introduced into the broken stone layer 22703. However, an apertured plate may be placed on the bottom of the soil layer 22701 to define a space below the soil layer 22701, and contaminated air may be introduced into the space.

While a portion of the pipe 221 and the fan 225 are overground in the second embodiment, the fan 225 may be placed in the space 217 or embedded in the planted zone 219, or the pipe 221 and the fan 225 may entirely be embedded underground.

The apertures 21101 of the apertured plate 211 may be of any of various desired shapes.

A planted zone in a park located near the road 201 or in a medial divider of the road 201 may be used as the planted zone 219.

A contaminated air purifying apparatus according to a third embodiment of the present invention will be described below with reference to FIGS. 7 through 9.

Figure 7:
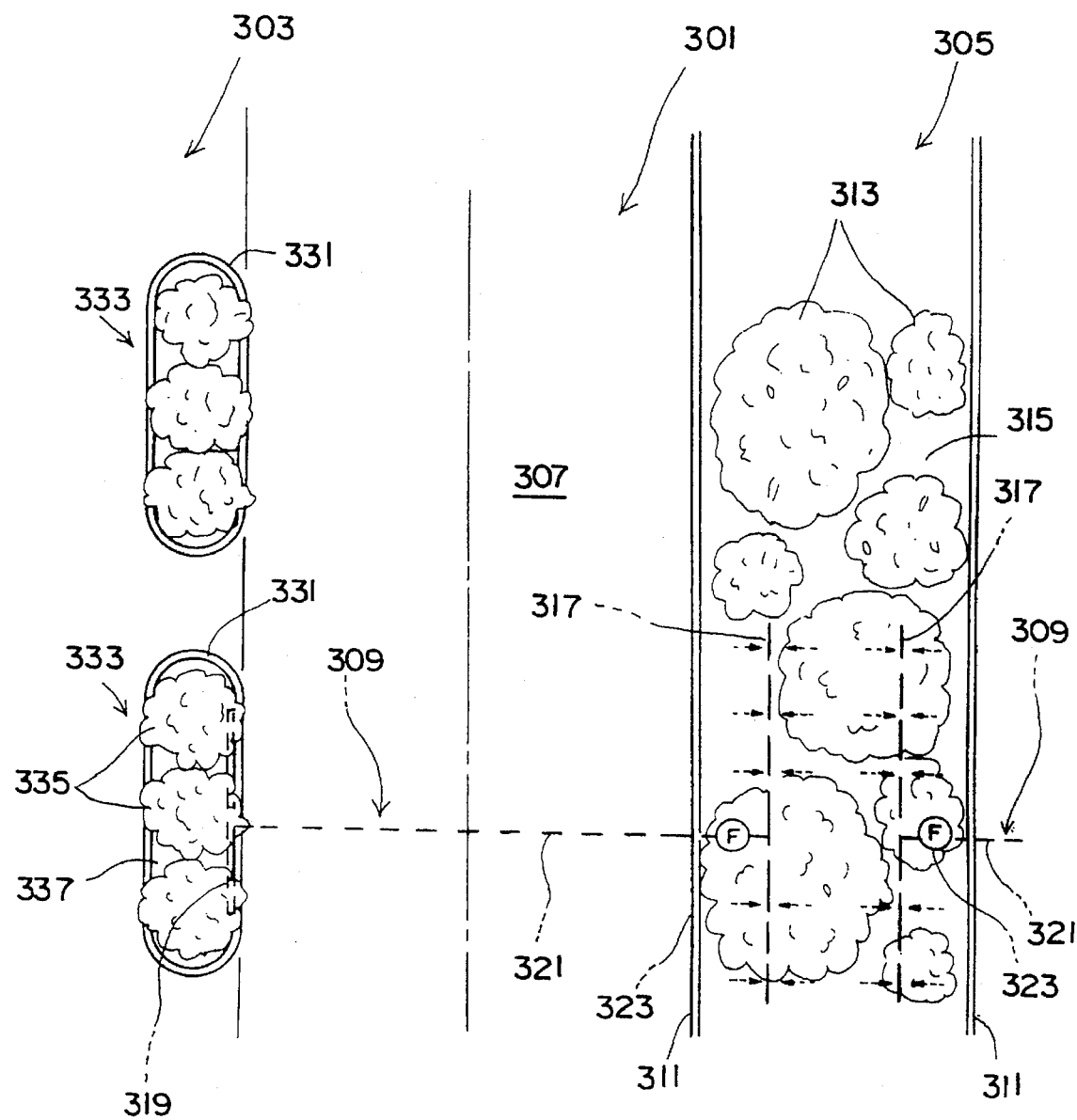
FIG. 7 is a fragmentary plan view of an automobile road and a sidewalk which incorporate a contaminated air purifying apparatus according to a third embodiment of the present invention.
Figure 8:
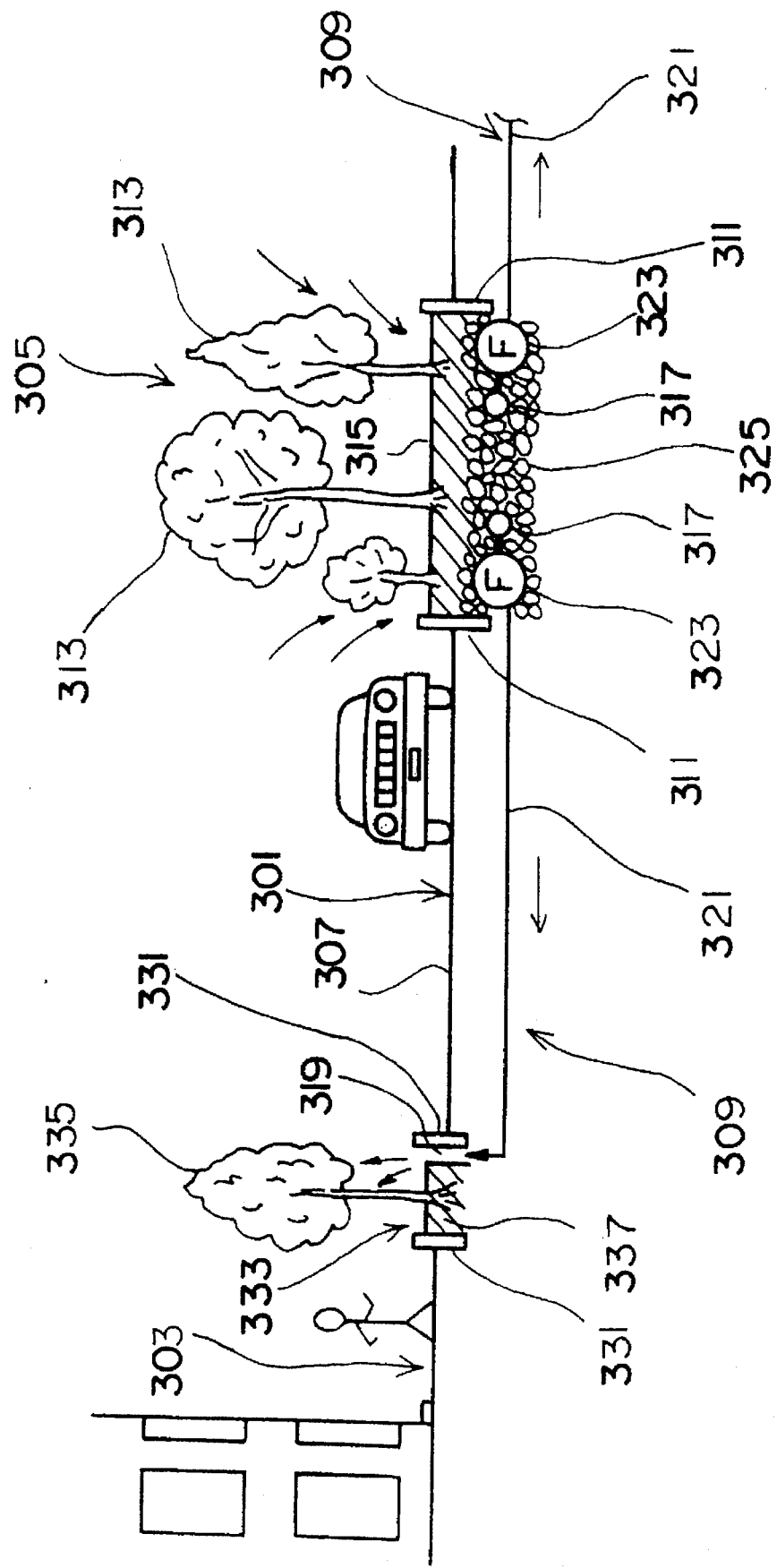
FIG. 8 is a vertical cross-sectional view of the automobile road and the sidewalk which incorporate the contaminated air purifying apparatus according to the third embodiment of the present invention.

As shown in FIGS. 7 and 8, a pair of contaminated air purifying apparatus, generally denoted at 309, according to the third embodiment of the present invention is combined with an automobile road 301, a pair of sidewalks 303, and a median strip 305 on the automobile road 301, the automobile road 301 having a pavement 307. The sidewalks 303 are positioned one on each side of the automobile road 301. The contaminated air purifying apparatus 309 extend between the median strip 305 and the sidewalks 303.

The median strip 305 is divided from the pavement 307 by a pair of curbs 311 located nearly at the center of the pavement 307, and includes a soil bed 315 extending between the curbs 311 and having planted trees 313.

Each of the contaminated air purifying apparatus 309 is composed of the soil bed 315 with the planted trees 313, an apertured pipe 317 embedded in the soil bed 315 near its bottom, an air outlet port 319 defined in one of the sidewalks 303, a joint pipe 321 interconnecting the apertured pipe 317 and the air outlet port 319, and a fan 323 disposed in the joint pipe 321. The apertured pipe 317 serves as an air inlet.

The soil bed 315 includes an soil layer which comprises a layer of soil for populating microorganisms therein, e.g., a layer of andosols. The soil is mixed with perlite or the like for a high degree of porosity or voidage, so that air can flow vertically through the soil layer.

The soil bed 315 also includes a broken stone layer 325 disposed underneath the soil layer near the bottom of the soil bed 315. The apertured pipe 317 is embedded in the broken stone layer 325 at its vertically intermediate region.

The respective apertured pipes 317 of the contaminated air purifying apparatus 309 are positioned closely to and extend along the respective curbs 311.

Each of the apertured pipes 317 comprises a pipe having a number of holes defined in its circumferential wall, and has a diameter ranging from about 300 to 400 mm and a length of about 50 m.

Figure 9:
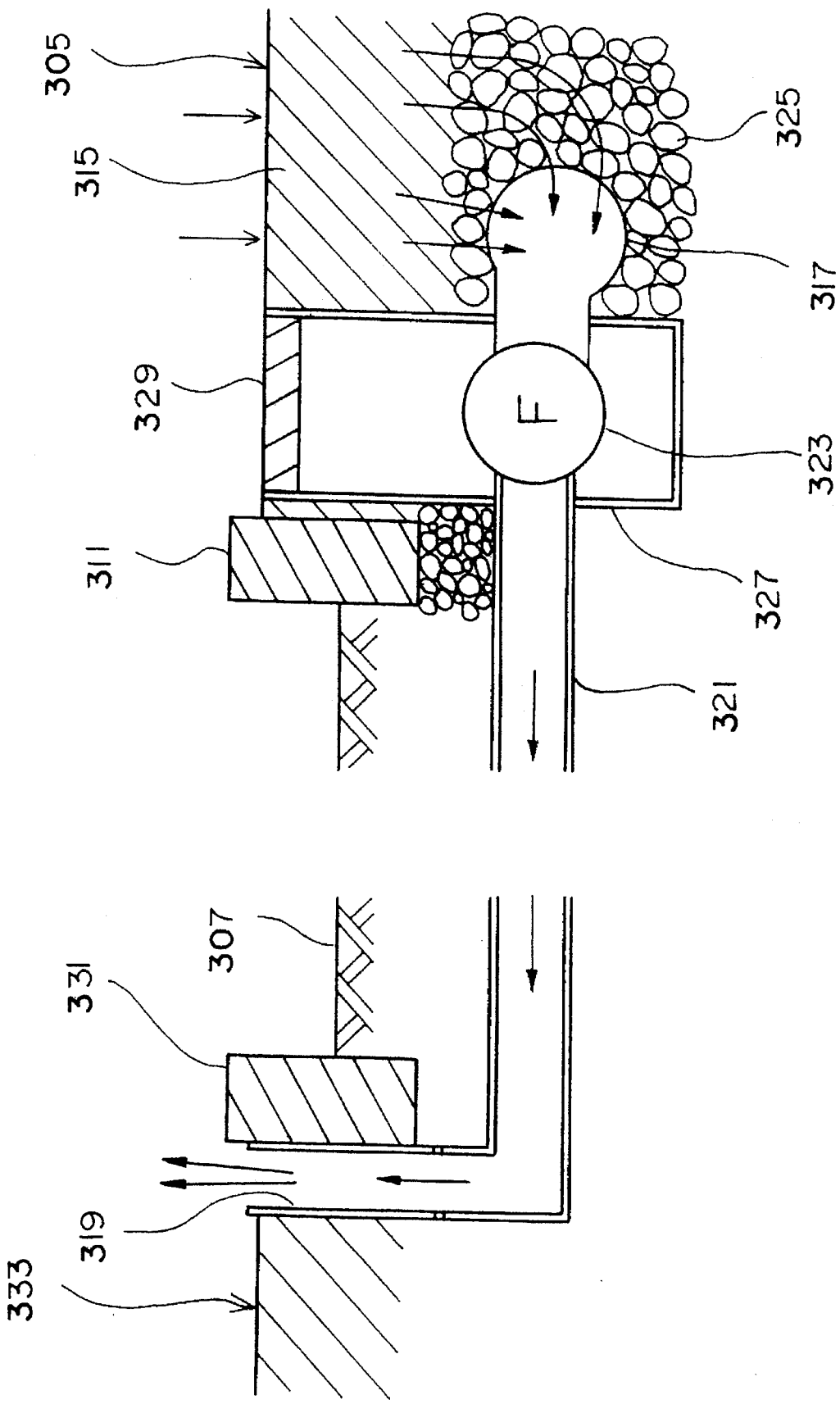
FIG. 9 is an enlarged fragmentary vertical cross-sectional view of the contaminated air purifying apparatus according to the third embodiment of the present invention.

As shown in FIG. 9, a box 327 is embedded in the soil bed 315 between each of the curbs 311 and the corresponding apertured pipe 317 at its longitudinally central region. The joint pipe 321 extends in a watertight manner through the box 327 from the longitudinally central region of the apertured pipe 317, runs below the pavement 307 toward the sidewalk 303.

The fan 323 is connected to the portion of the pipe 321 which is positioned in the box 327. The box 327 has an upper opening which is openably closed by a lid 329.

As shown in FIGS. 7 and 8, the sidewalk 303 has a series of planted zones 333 each of an oblong shape defined by a curb 331.

Each of the planted zones 333 is composed of trees 335 and a soil layer 337 with the air outlet port 319 embedded in the soil layer 337 near the pavement 307.

The air outlet port 319 opens upwardly and extends horizontally along the curb 331. The joint pipe 321 has an end bent upwardly below the soil layer 315 and connected to the air outlet port 319.

Each of the contaminated air purifying apparatus 309 operates as follows:

A power supply (not shown) is connected to rotate the fan 323. When the fan 323 is rotated, air in the broken stone layer 325 is drawn through the apertured pipe 317 into the joint pipe 321, and then discharged into the atmosphere from the air outlet port 319.

When the air is drawn from the broken stone layer 325, contaminated air is introduced from the upper surface of the soil bed 315, and flows through the soil bed 315 toward the broken stone layer 325.

Upon passage of the contaminated air through the soil bed 315, the contaminated air is purified thereby in the same manner as with the first and second embodiments described above, and clean air from which contaminants have been removed is discharged from the air outlet port 319 into the atmosphere over the sidewalk 303.

In the third embodiment, contaminated air is purified by the trees 313 and the soil bed 315 on the median strip 305, and clean air is discharged over the sidewalk 303. Therefore, clean air is supplied to the sidewalk 303 along the automobile road 1, and people walking on the sidewalk 303 can inhale the supplied clean air. The supplied clean air is effective to make the people walking on the sidewalk 303 feel comfortable.

In the third embodiment, since air flows from the surface of the soil bed 315 toward the air outlet port 319, the lower portion of the soil bed 315 is composed of the broken stone layer 325, and the apertured pipe 317 is embedded in the broken stone layer 325. However, an apertured plate may be placed near the bottom of the soil bed 315 to define a space below the soil layer thereof, and air may be introduced from the space into the joint pipe 321.

If the apertured pipe 317 comprises a pipe having a number of apertures defined only in a lower circumferential wall thereof, then rainwater is prevented from entering the apertured pipe 317 and the apertured pipe 317 needs no water drainage.

The air outlet port 319 may be of any of various desired shapes.

Figure 10:
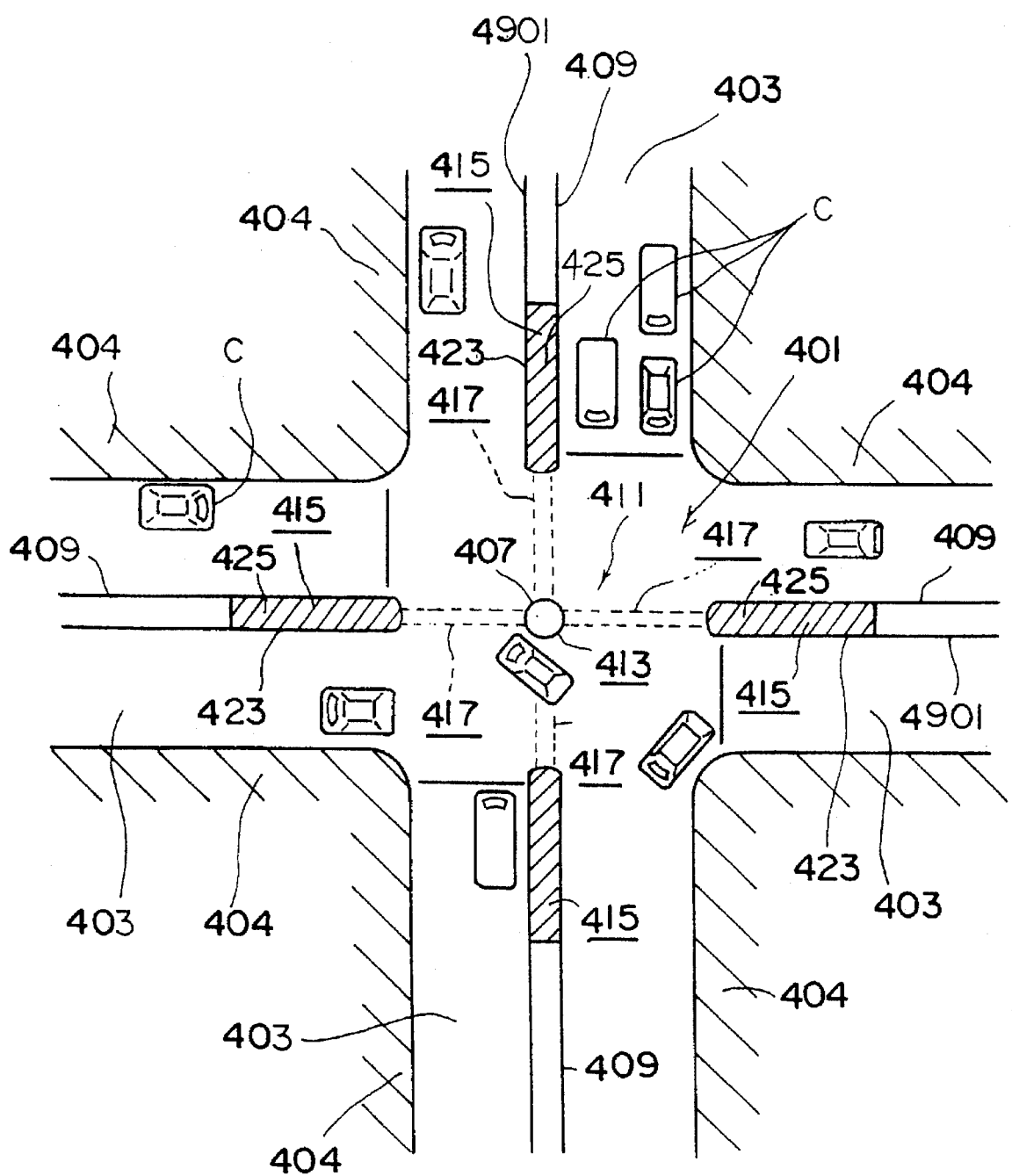
FIG. 10 is a plan view of an intersection which incorporates a contaminated air purifying apparatus according to a fourth embodiment of the present invention.
Figure 11:
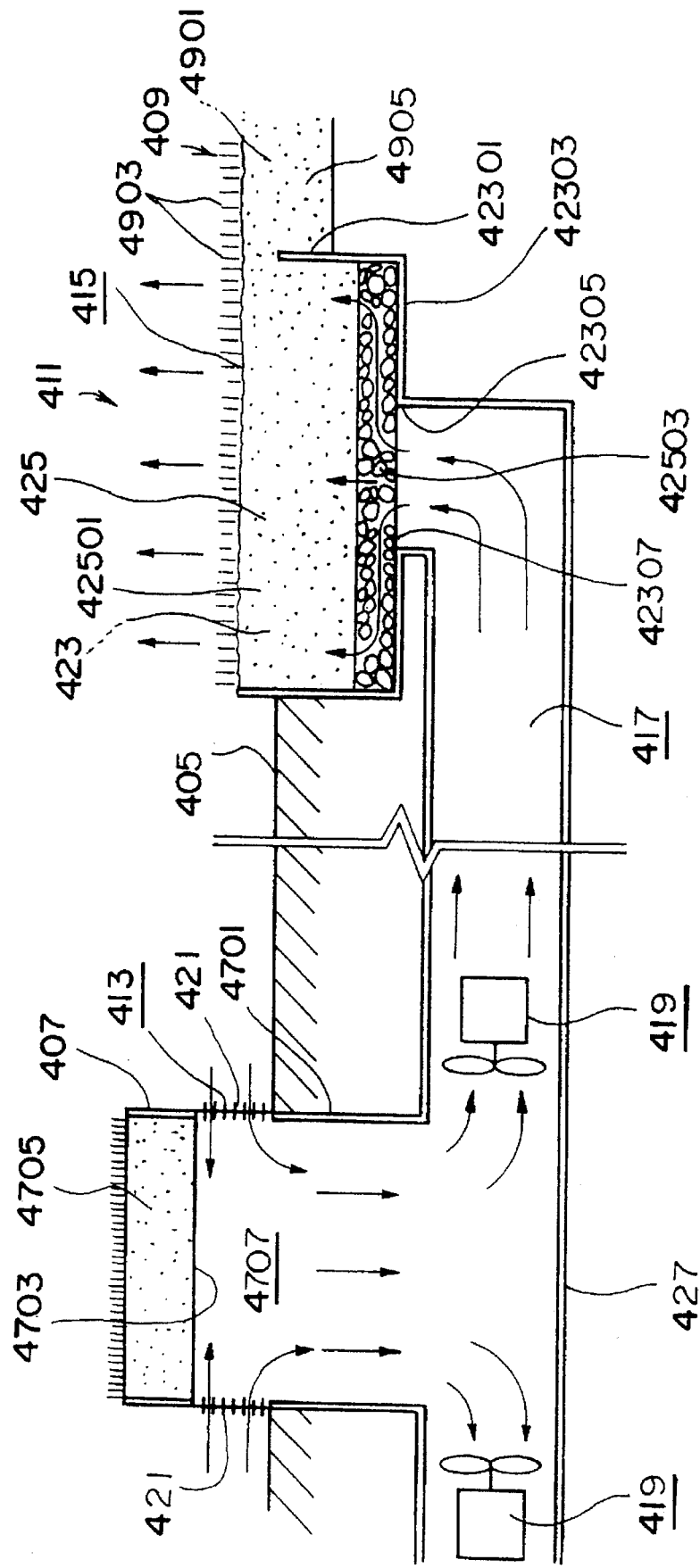
FIG. 11 is a vertical cross-sectional view of the intersection which incorporates the contaminated air purifying apparatus according to the fourth embodiment of the present invention.

FIGS. 10 and 11 show a contaminated air purifying apparatus according to a fourth embodiment of the present invention which is incorporated in an intersection.

As shown in FIGS. 10 and 11, the contaminated air purifying apparatus, generally denoted at 411, according to the fourth embodiment of the present invention is combined with an intersection 401 connecting roads 403 with sidewalks 404, the roads 403 having road surfaces 405. A cylindrical tower 407 having a relatively small height is positioned at the center of the intersection 401 for allowing automobiles C to change their course smoothly. Each of the roads 403 has a median strip 409 in its transversely central region.

The contaminated air purifying apparatus 411 is located between the tower 407 and the median strips 409.

The contaminated air purifying apparatus 411 comprises an air inlet port 413, a plurality of air outlet ports 415, a plurality of air passages 417 communicating between the air inlet port 413 and the air outlet ports 415, and a plurality of fans 419 disposed in the respective air passages 417.

The tower 407 comprises a vertical cylindrical concrete body 4701 having a lower portion embedded in the intersection 401. A bottom plate 4703 is horizontally disposed in an upper portion of the concrete body 4701 above the ground level, and a soil layer 4705 with cultivated plants is placed on the bottom plate 4703.

The portion of the concrete body 4701 underneath the bottom plate 4703 has a space 4707 defined therein. The concrete body 4701 has a plurality of circumferentially spaced windows 421 defined in its wall which lies below the bottom plate 4703 and is exposed over the road surface 405. The windows 421 serve as the air inlet port 413.

Each of the median strips 409 has a first soil container 4901 which is elongate along the road 403, and a soil layer 4905 housed in the first soil container 4901 and having cultivated plants 4903. Each of the median strips 409 also has a second soil container 423 located more closely to the intersection 401 than the first soil container 4901 and contiguous to an upper portion of the first soil container 4901.

The second soil container 423 comprises side walls 42301 of concrete and a bottom wall 42303 of concrete. The bottom wall 42303 has a central hole 42305 defined therein.

An air-permeable member 42307 such as a metal mesh or an apertured plate for allowing air to flow therethrough is disposed on the bottom wall 42303 over the central hole 42305. The second soil container 423 houses a soil bed 425 placed on the air-permeable member 42307 and having plants 4903 cultivated thereon. The soil bed 425 has an upper surface lying substantially flush with the upper surface of the soil layer 4905 in the first soil container 4901.

The soil bed 425 comprises a soil layer 42501 and a broken stone layer 42503 disposed underneath the soil layer 42501.

The soil layer 42501 comprises a layer of soil for populating microorganisms therein, e.g., a layer of andosols, so that air can flow vertically through the soil layer 42501. The broken stone layer 42503 comprises a number of broken or crushed stones. The second soil container 423 and the soil bed 425 with the cultivated plants 4903 jointly serve as the air outlet pot 415.

A pipe 427 extends underground below the road surface 405 and provides communication between the space 4707 in the concrete body 4701 and the hole 42305 in the bottom wall 42303 of the second soil container 423 of each of the median strips 409. The pipe 427 serves as the air passage 417, and each fan 419 is disposed in the pipe 427.

Operation of the contaminated air purifying apparatus 411 will be described below.

A power supply (not shown) is connected to rotate each of the fans 419. When each fan 419 is rotated, contaminated air around the tower 407 is drawn through the windows 421 into the concrete body 4701, flows through the space 4707, the pipe 427, and the hole 42305 into the bottom of each second soil container 423.

The contaminated air then passes through the broken stone layer 42503 and the soil layer 42501, which purify the contaminated air in the same manner as the first through third embodiments described above, and clean air from which contaminants have been removed is discharged from each median strip 409 into the atmosphere over the road 403.

In the fourth embodiment, contaminated air in the intersection 401 is drawn into the tower 407 located at the center of the intersection 401 and led underground to the median strips 409. The contaminated air is then purified by the soil beds 427 in the median strips 409, and produced clean air is discharged from the median strips 409 into the atmosphere over the roads 403. The contaminated air purifying apparatus 411 can be installed without impairing the appearance of the intersection 401 and the roads 403 and also without the need for a special extra space on the intersection 401, the roads 403, and the sidewalks 404, and can reliably purify contaminated air present in the intersection 401.

The air inlet port 413 is not limited to the illustrated location or structure, and may be located or structured as desired. For example, an air inlet port may be incorporated in a traffic signal, or in a footbridge that may be installed at the intersection 401. Alternatively, a hole may be defined in the intersection 401 itself or the road surfaces 405 near the intersection 401, and may be covered with a grating for use as the air inlet port.

Each of the air outlet ports 415 is not limited to the illustrated location or structure, and may be located or structured as desired. For example, a planted zone which may be provided on each of the sidewalks 404 may be used as the air outlet port.

A contaminated air purifying apparatus according to a fifth embodiment of the present invention, which is incorporated in a three-dimensional structure such as a station terminal, will be described below with reference to FIG. 12.

Figure 12:
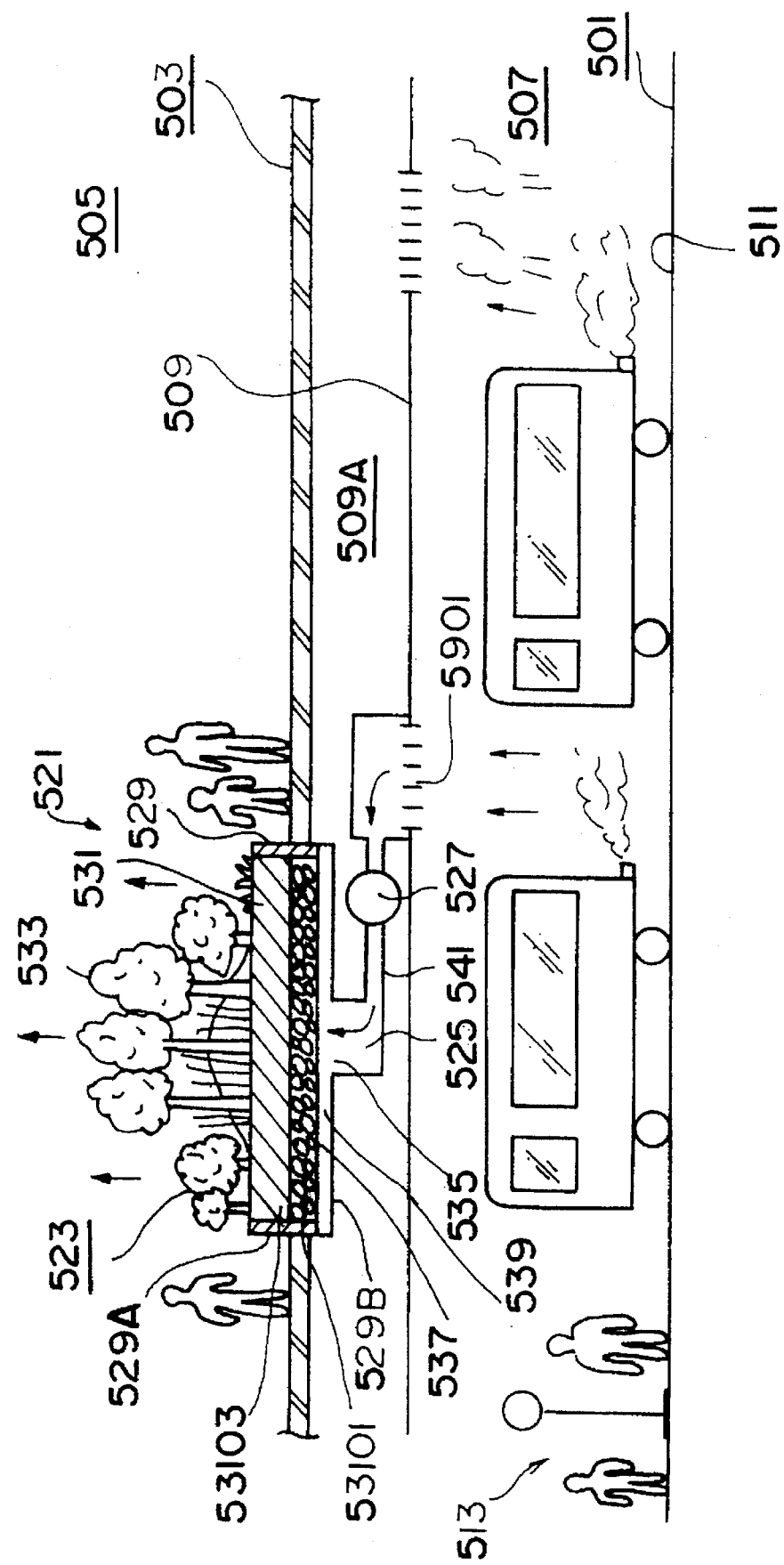
FIG. 12 is a vertical cross-sectional view of a three-dimensional structure which incorporates a contaminated air purifying apparatus according to a fifth embodiment of the present invention.

As shown in FIG. 12, an artificial foundation 503 is disposed over a ground level 501, and spaces 505, 507 are defined above and below the artificial foundation 503. The space 505 is vented to the atmosphere.

A ceiling 509 is disposed below the artificial foundation 503. The space 507 below the artificial foundation 503 is defined between the ceiling 509 and the ground level 501. A road 511 is constructed on the ground level 501, and a bus stop 513 is positioned on one side of the road 511. The ground level 501 may be in the form of either an artificial foundation or a natural foundation.

The contaminated air purifying apparatus, generally denoted at 521, according to the fifth embodiment of the present invention includes a planted zone 523 mounted on the artificial foundation 503, an air passage 525 communicating between the planted zone 523 and the space 507, and a fan 527 disposed in the air passage 525.

The planted zone 523 comprises a soil container 529 mounted on the artificial foundation 503 and composed of side walls 529A and a bottom wall 529B, a soil bed 531 accommodated in the soil container 529, and plants 553 cultivated on the soil bed 531.

The bottom wall 529B has a central hole 535 defined therein. An air-permeable member 537 such as a metal mesh or an apertured plate for allowing air to flow therethrough is disposed above the bottom wall 529B over the central hole 535. The soil bed 531 is disposed on the air-permeable member 537. A flat space 539 is defined between the air-permeable member 537 and the bottom wall 529B.

The soil bed 531 comprises a broken stone layer 53101 disposed on the air-permeable member 537 and a soil layer 53103 disposed on the broken stone layer 53101.

The broken stone layer 53101 comprises a number of broken or crushed stones. The soil layer 53103 comprises a layer of soil for populating microorganisms therein, e.g., a layer of andosols, so that air can flow vertically through the soil layer 53103.

The air passage 525 is defined by a duct 541 positioned in a space 509A defined between the artificial foundation 503 and the ceiling 509. The duct 541 has an end connected to a ventilation hole 5901 defined in the ceiling 509 and an opposite end connected to the hole 535, and the fan 527 is disposed in the duct 541.

Operation of the contaminated air purifying apparatus 521 will be described below.

A power supply (not shown) is connected to rotate the fan 527. When the fan 527 is rotated, air in the space 507 which has been contaminated by exhaust gases emitted from automobiles is drawn from the ventilation hole 5901, flows through the duct 541, and is discharged into the space 539 below the soil bed 531.

The contaminated air then passes through the broken stone layer 53101 and the soil layer 53103, which purify the contaminated air in the same manner as the previous embodiments described above, and clean air from which contaminants have been removed is discharged from the planted zone 523 into the space over the artificial foundation 505.

In the fifth embodiment, contaminated air in the space 507 below the artificial foundation 503 is led into the planted zone 523 on the artificial foundation 503, and purified by the planted zone 523. Since the planted zone 523 which is originally placed on the artificial foundation 503 or on a side of a sidewalk without concern for air purification can be used to purify contaminated air, the contaminated air purifying apparatus 521 can be installed without the need for a special installation space and without impairing the appearance of surroundings. Stated otherwise, it is possible to purify contaminated air in the space 507 below the artificial foundation 503 without the need for a special installation space and without impairing the appearance of surroundings.

Figure 13:
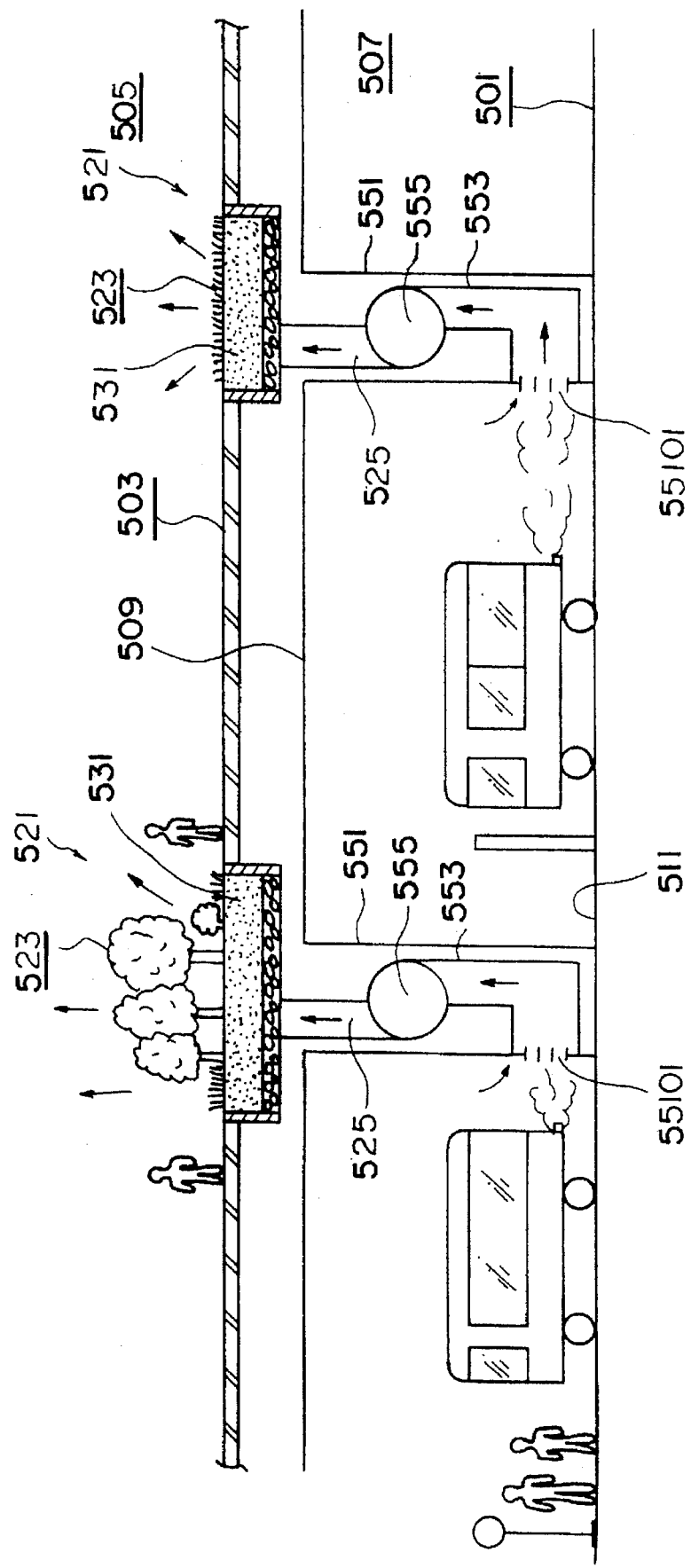
FIG. 13 is a vertical cross-sectional view of a three-dimensional structure which incorporates a modified contaminated air purifying apparatus.

FIG. 13 shows in vertical cross section a three-dimensional structure which incorporates a modified contaminated air purifying apparatus according to the present invention.

As shown in FIG. 13, posts 551 are disposed between a ground level 501 and an artificial foundation 503 spaced upwardly therefrom. Each of the posts 551 houses therein a vertical duct 553 which defines an air passage 525. The other structural details of the modified contaminated air purifying apparatus shown in FIG. 13 are essentially the same as those of the contaminated air purifying apparatus shown in FIG. 12.

Each of the ducts 553 has a lower end connected to an opening 55101 defined in a side wall of a lower end of the post 551, and an upper end connected to the bottom of the soil bed 531. Contaminated air in the space 507 is delivered by a fan 555 in the duct 553 from the opening 55101 through the duct 553 to the bottom of the soil bed 531, which then purifies the contaminated air. Clean air from which contaminants have been removed is discharged from each planted zone 523 into the space 505 above the artificial foundation 503.

Figure 14:
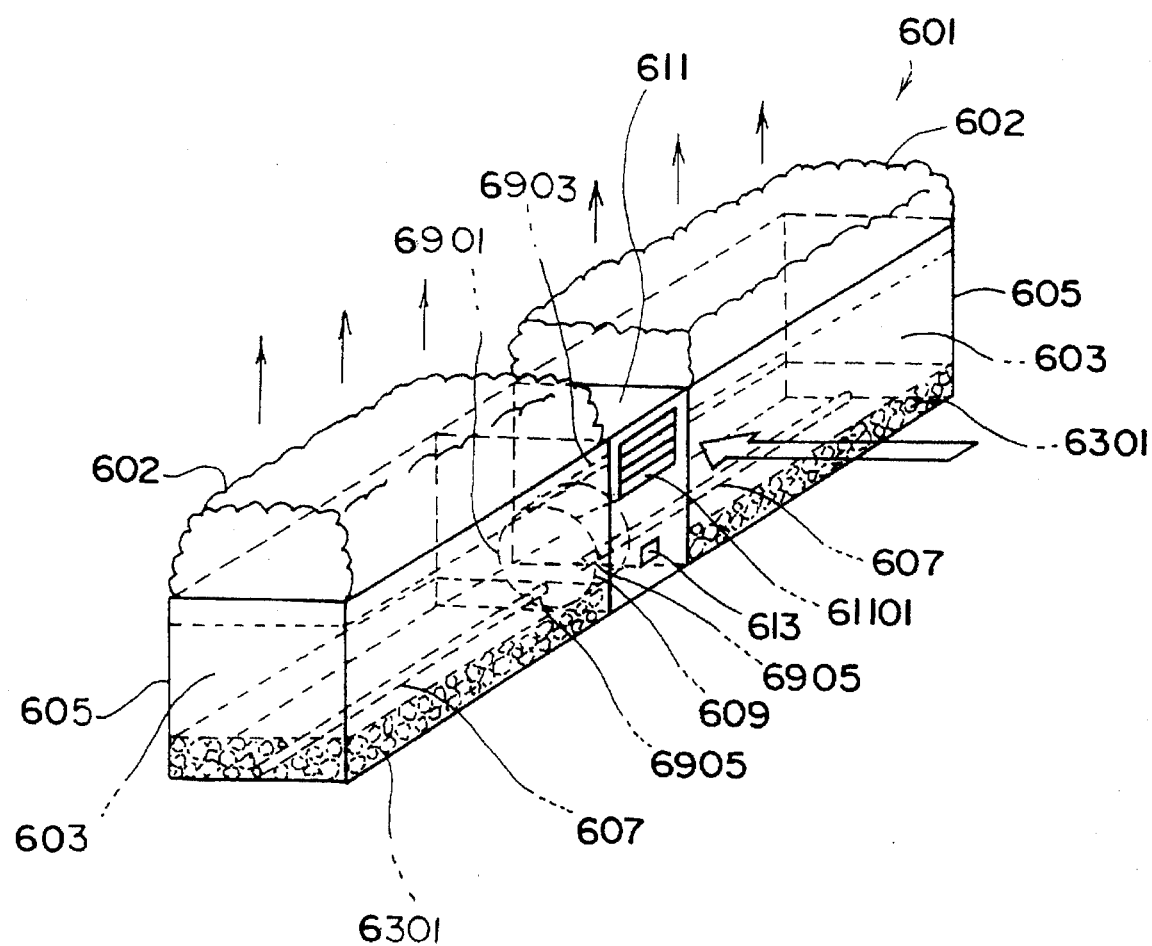
FIG. 14 is a perspective view of a contaminated air purifying apparatus according to a sixth embodiment of the present invention.
Figure 15:
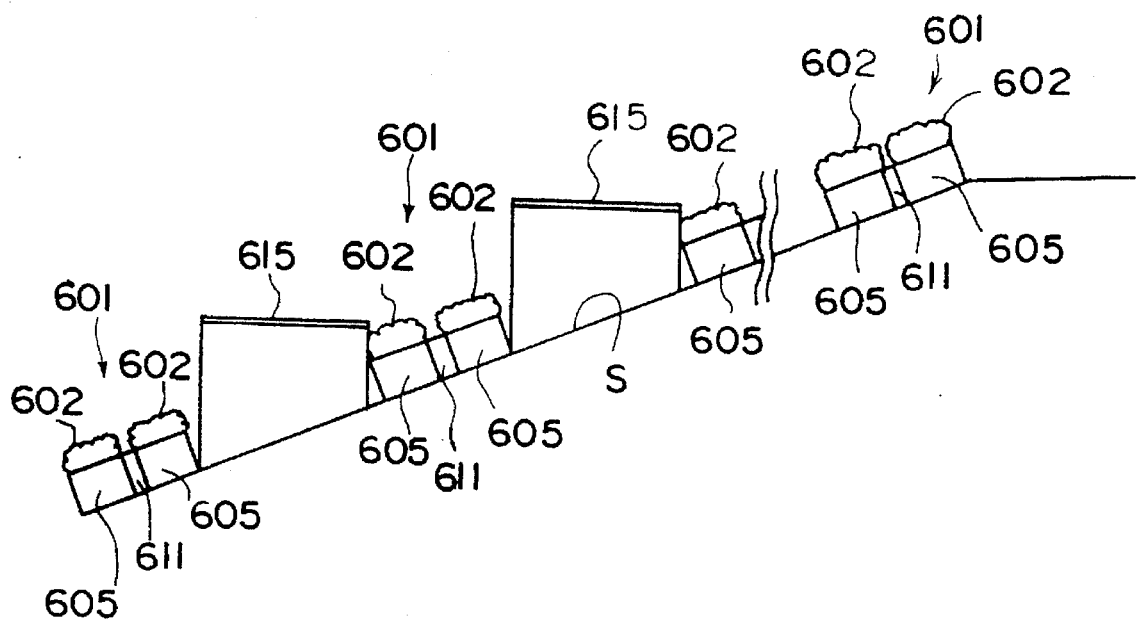
FIG. 15 is a front elevational view showing the manner in which the contaminated air purifying apparatus according to the sixth embodiment of the present invention are used.
Figure 16:
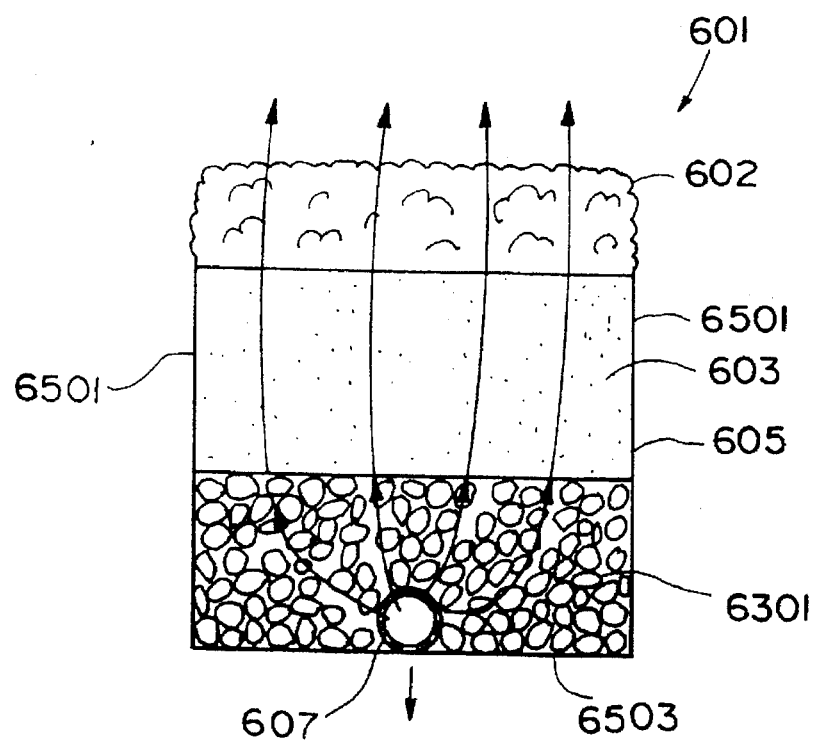
FIG. 16 is a transverse cross-sectional view of the contaminated air purifying apparatus according to the sixth embodiment of the present invention.

FIGS. 14 through 16 illustrate a contaminated air purifying apparatus according to a sixth embodiment of the present invention.

As shown in FIG. 15, a plurality of contaminated air purifying apparatus 601 according to the sixth embodiment of the present invention are arrayed alongside a slope S which interconnects a road and an underground parking lot.

As shown in FIG. 14, each of the contaminated air purifying apparatus 601 comprises a pair of soil beds 603 with cultivated plants 602, a pair of soil containers 605 which accommodate the soil beds 603, respectively, a pair of apertured pipes 607 defining respective air passages for introducing contaminated air into bottoms of the soil beds 603, an air blower (air flowing means) 609 for drawing and supplying contaminated air to the apertured pipes 607, and a case 611 disposed between the soil containers 605 and housing the air blower 609.

Each of the soil beds 603 comprises a layer of soil for populating microorganisms therein, e.g., a layer of andosols mixed with perlite and so on for a high degree of porosity or voidage, and a gravel layer 6301 composed of broken or crushed stones and positioned underneath the layer of soil. The apertured pipes 607 are embedded in the gravel layers 6301, respectively, of the soil beds 603.

Each of the containers 605 is in the form of an elongate rectangular parallelepiped and has four side walls 6501 and a bottom wall 6503 joined to and lying between the lower ends of the side walls 6501.

The containers 605 which accommodate the soil beds 603 with the cultivated plants 602 and the case 611 which houses the air blower 609 are movable together. The containers 6705 are arrayed in their longitudinal direction, with the case 611 interposed therebetween.

The case 611 and the containers 605 have the same width and height. The case 611 has an air inlet port 61101 defined in an upper front wall portion thereof for drawing contaminated air.

The air blower 609 comprises a casing 6901 housing a fan (not shown), a suction pipe 6903 extending from the casing 6901, and two discharge pipes 6905 projecting from opposite side of the casing 6901. The suction pipe 6903 has a distal end connected to the air inlet port 61101, and the two discharge pipes 6905 are connected to ends of the respective apertured pipes 607. The containers 605 which accommodate the soil beds 603 with the cultivated plants 602 and the case 611 which houses the air blower 609 are combined as a unit.

As shown in FIG. 14, the case 611 has a sensor 613 mounted on a lower front wall portion thereof for detecting whether an automobile has moved past the sensor 613. When the sensor 613 detects that an automobile has moved past the sensor 613, the sensor 613 issues a signal to actuate the air blower 609 for a predetermined period of time.

As shown in FIG. 15, a plurality of solar panels 615 each having solar cells are placed on the slope S, each between two contaminated air purifying apparatus 601. The air blowers 609 are actuated by the electric energy which is generated by the solar cells of the solar panels 615.

Water drainage pipes of the water-seal-trap type are disposed respectively at the four corners of the bottom wall of each of the containers 605 for draining water when an excessive amount of water is introduced into the container 605 while preventing unpurified air from escaping through the water drainage pipes.

Operation of the contaminated air purifying apparatus 601 will be described below.

When an automobile runs along the slope S, its passage is detected by the sensor 613, actuating the air blower 609.

When the air blower 609 is actuated, air contaminated by exhaust gases emitted by the automobile is drawn in from the air inlet port 61101 through the suction pipe 6903 and supplied from the discharge pipes 6905 into the corresponding apertured pipes 907.

The contaminated air flows from the apertured pipes 907 through the gravel layers 6301 and then the soil layers thereon.

When the contaminated air passes through the soil beds 603, it is purified by the soil beds 603 in the same manner as with the previous embodiments. Clean air from which contaminants have been removed is discharged from the surface of the soil beds 603 between the plants 602 into the atmosphere.

In the sixth embodiment, since contaminated air is purified using the soil beds 603 with the cultivated plants 602, and no special air purifiers are installed, but trees and flower beds may be combined with the contaminated air purifying apparatus 601, the contaminated air purifying apparatus 601 can be installed without impairing the appearance of surroundings.

The plants 602 and the soil can be replaced as desired. Particularly, replacement of the plants 602 may be effective to make the contaminated air purifying apparatus 601 sightly.

The air blower 609 is actuated by the electric energy which is generated by the solar cells of the solar panels 615. Alternatively, the air blower 609 may be actuated by a commercial power supply.

While the air passage is defined by the apertured pipe 607 in this embodiment, it may be defined by a space created below and coextensive with each of the bottom walls 6503, or may be of any structure insofar as contaminated air can be supplied therefrom to the bottom of the soil bed 603.

In the illustrated six embodiment, the case 611 housing the air blower 609 is separate from and disposed on one side of the containers 605. However, the containers 605 and the case 611 may be integral with each other, or the air blower 609 may be disposed in a space created in a lower portion of each of the containers 605. Alternatively, the air blower 609 may be located away from the containers 605. The latter alternative modification needs a long air passage interconnecting the air blower 609 to the bottom of the soil beds 603.

The contaminated air purifying apparatus 601 may be installed anywhere indoors or outdoors. For example, it may be installed outdoors on a median strip of a major road, a parking lot, or a sidewalk at an intersection or along a department store where a traffic jam is likely to happen.

In the illustrated sixth embodiment, contaminated air passes through each soil bed 603 from its bottom toward its upper surface, and clean air is returned from the upper surface of the soil bed 603 to the atmosphere. However, the air flow may be reversed by drawing contaminated air from the upper surface of the soil bed 603 toward the bottom thereof with a suction pump that may be disposed in the case 611 in place of the air blower 609, and returning clean air that has passed through the soil bed 603 from the case 611 back to the atmosphere.

Figure 17:
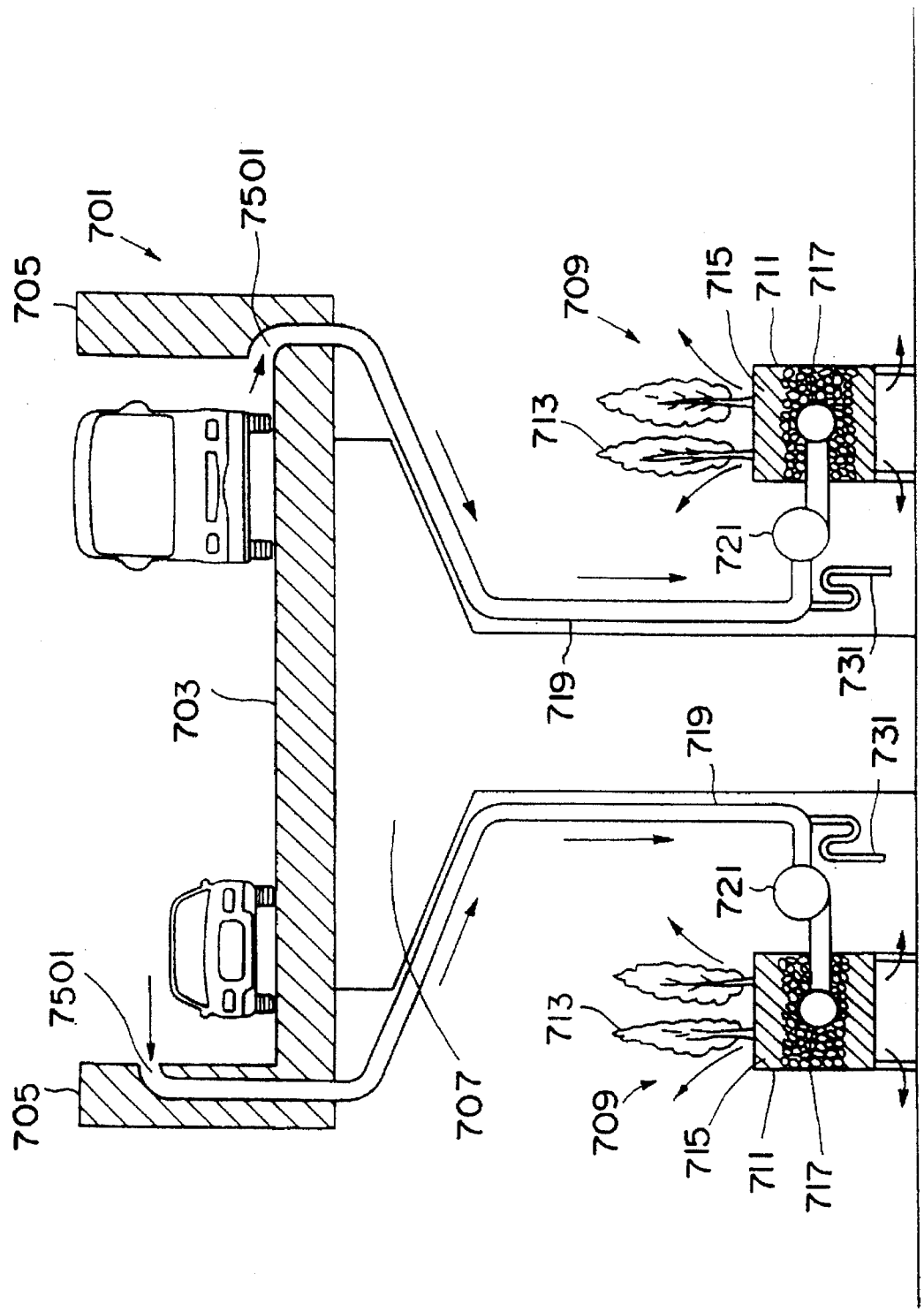
FIG. 17 is a vertical cross-sectional view of contaminated air purifying apparatus according to a seventh embodiment of the present invention.
Figure 18:
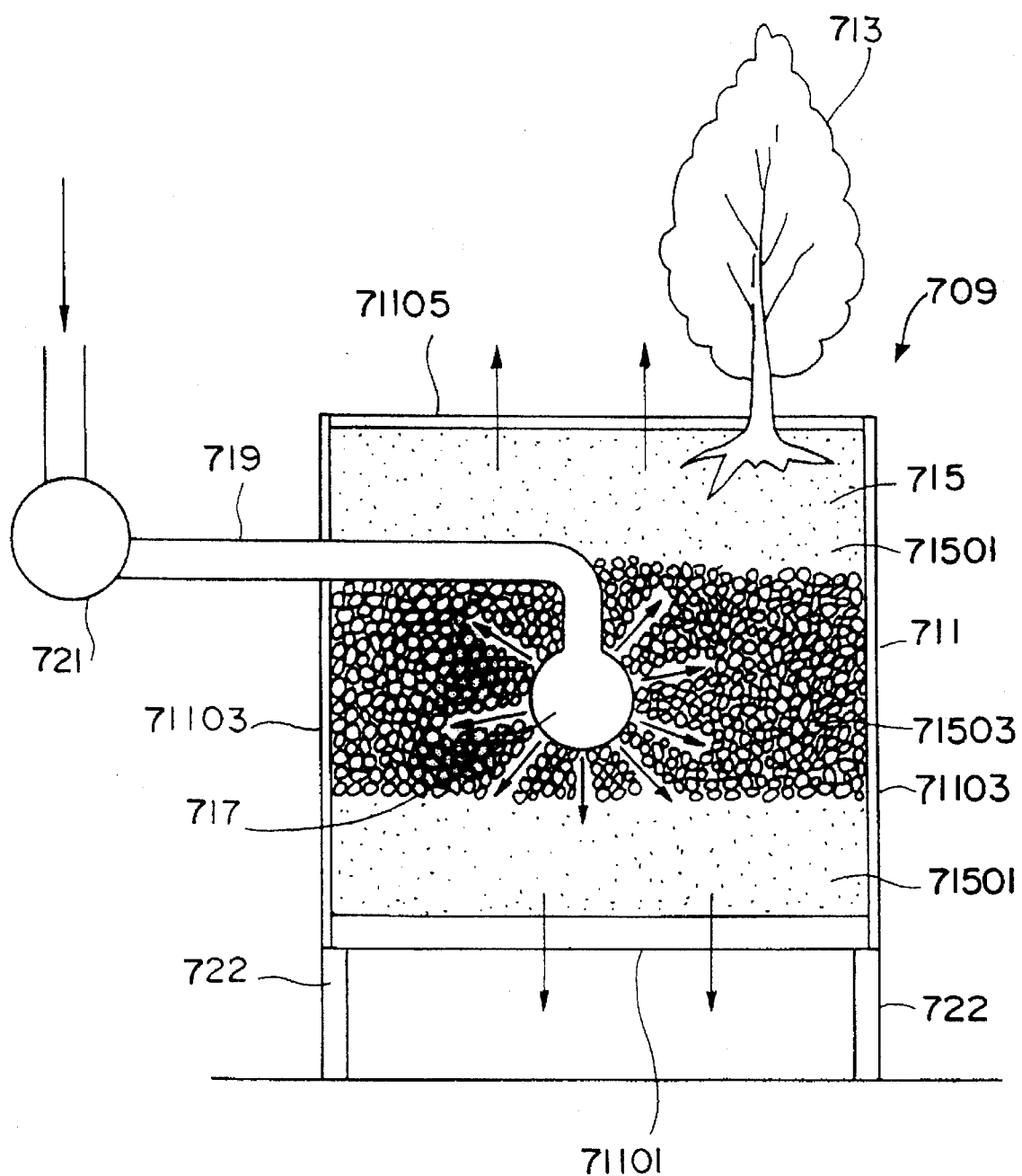
FIG. 18 is an enlarged vertical cross-sectional view of the contaminated air purifying apparatus according to the seventh embodiment of the present invention.

FIGS. 17 and 18 show in vertical cross section contaminated air purifying apparatus according to a seventh embodiment of the present invention. The contaminated air purifying apparatus according to the seventh embodiment of the present invention are combined with an elevated road.

As shown in FIG. 17, an elevated road 701 having a road surface 703 and a pair of sound-insulating side walls 705 is supported on piers 707. Pairs of contaminated air purifying apparatus 709 are combined with the elevated road 701 at certain intervals along the elevated road 701. The contaminated air purifying apparatus 709 in each pair are mounted on a ground level below the elevated road 701 one on each side of the elevated road 701.

As shown in FIG. 18, each of the contaminated air purifying apparatus 709 comprises a case 711, a soil bed 715 housed in the case 711 and having cultivated plants 713, an air outlet 717 embedded in the soil bed 715, a pipe 719 connected to the air outlet 717, and a fan 721 disposed in the pipe 719.

The case 711 is of a rectangular shape as viewed in plan, and comprises a bottom wall 71101, four side walls 71103, and a top wall 71105, the case 711 having a predetermined volume. The bottom wall 71101 is composed of an air-permeable member such as a punched metal sheet. The top wall 71105 is composed of a frame-like open member through the plants 713 can extend upwardly. The case 711 is supported at a height above the ground level by legs 722.

The soil bed 715 comprises a pair of soil layers 71501 positioned immediately above and below the bottom and top walls 71101, 71105, respectively, and a broken stone layer 71503 positioned between the soil layers 71501.

Each of the soil layers 71501 comprises a layer of soil for populating microorganisms therein, e.g., a layer of andosols, so that air can flow vertically through the soil layer 71501. The broken stone layer 71503 comprises a number of broken or crushed stones or rock fragments.

The air outlet 717 is embedded in the broken stone layer 71503. The air outlet 717 is defined by a hollow spherical member having a number of holes defined in its wall, and the pipe 719 has an end connected to the hollow spherical member.

The pipe 719 extends hermetically horizontally through one of the side walls 71103 of the case 711, and also extends vertically upwardly along one of the piers 707. The pipe 719 has an upper end connected to a hole 7501 defined in one of the side walls 705. The pipe 715 may be in the form of a drain gutter of the elevated road 701.

The hole 7501 may be defined in a lower portion or vertically intermediate portion of the side wall 705, and is in the shape of a horizontally elongate slit for easily drawing in contaminated air from the elevated road 701.

The fan 721 is disposed in the pipe 719 closely to the case 711. When the fan 721 is actuated, air flows from the hole 7501 through the pipe 719 toward the air outlet 717 in the case 711.

A water drainage pipe 731 of the water-seal-trap type is connected to the pipe 719 at its horizontal section.

Operation of each of the contaminated air purifying apparatus 709 according to the seventh embodiment of the present invention will be described below.

A power supply (not shown) is connected to rotate the fan 721. When the fan 721 is rotated, air in the atmosphere above the elevated road 701, which has been contaminated by exhaust gases emitted from automobiles, is drawn from the hole 7501 into the pipe 719, and introduced from the air outlet 717 into the broken stone layer 71503. The contaminated air then flows through the broken stone layer 71503 and the soil layers 71501, and is discharged out of the case 711 from the top and bottom walls 71105, 71101.

When the contaminated air passes through the broken stone layer 71503 and the soil layers 71501, the broken stone layer 71503 and the soil layers 71501 purify the contaminated air in the same manner as the previous embodiments described above, and clean air from which contaminants have been removed is discharged out of the case 711.

Since each of the contaminated air purifying apparatus 709 employs the soil beds 715, it is inexpensive to manufacture and easy to maintain.

Because each of the contaminated air purifying apparatus 709 employs the soil beds 715, it may have the appearance of a planted structure with the cultivated plants 713 and hence can be installed without making nearby regions unsightly.

The contaminated air introduced from the air outlet 717 into the soil bed 715 passes through the broken stone layer 71503 and the soil layers 71501, and is then discharged upwardly from the case 711 and downwardly from the case 711. Since the contaminated air flows in two opposite vertical directions through the soil bed 715, the contaminated air can be purified by the soil bed 715 highly efficiently.

Any rainwater which may enter the case 711 can flow successively through the upper soil layer 71501, the broken stone layer 71503, and the lower soil layer 71501, and be discharged downwardly from the bottom wall 71101 because the bottom wall 71101 is air-permeable. Water in the case 711 can thus be drained easily and no special mechanism or structure for draining water is required in the case 711.

An experiment was conducted on the contaminated air purifying apparatus 709 as follows:

Each of the soil layers 71501 had a thickness of about 50 cm, and the broken stone layer 71503 was composed of broken stones or rock fragments and had a thickness of about 60 cm.

Each of the soil layers 71501 was composed of soil mixed with perlite and vermiculite for higher air and water permeability, and also with peat moss, leaf mold, and compost for a higher content of organic substances.

The broken stones or rock fragments of the broken stone layer 71503 were mixed with perlite for higher air and water permeability.

The pipe 719 had a diameter of about 300 mm.

The fan 721 had an air displacement capability of b $54c^3$/hr.

The average concentrations of NOx and CO over the elevated road 701 ware 0.35 ppm and 12.0 ppm, respectively, and the average concentrations of NOx and CO in the vicinity of the case 711 were 0.02 ppm and 0.58 ppm, respectively. Therefore, the removal ratio for NOx was 94%, and the removal ratio for CO was 95%.

In the seventh embodiment shown in FIGS. 17 and 18, the soil bed 715 is composed of the broken stone layer 71503 and the soil layers 71501, and contaminated air is introduced into the broken stone layer 71503. However, apertured plates may be placed between the soil layers 71501 to define a space therebetween, and the broken stone layer 71503 may be dispensed with, and clean air may be introduced into the space.

In the above embodiment, the contaminated air is divided into upward and downward streams in the soil bed 715.

However, the contaminated air may be divided into opposite horizontal streams in the soil bed 715. In such a modification, two confronting side walls of the case 711 are composed of air-permeable members. If the bottom wall 71101 and all the side walls 71103 are composed of air-permeable members, then the contaminated air can flow in various many directions in the case 711, and thus can be purified highly efficiently.

Those air-permeable members are not limited to members of a single type such as punched metal members, but may be a combination of members of different types.

While the contaminated air purifying apparatus 709 has been described as being used to purify contaminated air over the elevated road 701, the contaminated air purifying apparatus 709 may be used anywhere indoors or outdoors at areas where contaminated air is to be purified.

The air flow in the contaminated air purifying apparatus 709 may be reversed. For example, the contaminated air may be drawn in from the top and bottom walls 71105, 71101 of the case 711 into the air outlet 717, which now serves as an air inlet, and clean air may be discharged from the case 711 through the pipe 719.

Although certain preferred embodiments of the present invention has been shown and described in detail, it should be understood that various changes and modifications may be made therein without departing from the scope of the appended claims.

What is claimed is:

1. An apparatus for purifying contaminated air, comprising:

a road having a road surface;

an air inlet exposed to said road surface;

an air outlet spaced from said road surface;

a soil bed containing microorganisms populated therein for chemically degrading contaminant gases in contaminated air, said soil bed allowing air to pass therethrough; and air flowing means for introducing air into said soil bed through said air inlet, passing the air through said soil bed, and discharging the air from said soil bed through said air outlet;

a structure with a wall in which said air inlet is defined, said structure positioned at a center of an intersection connecting said road with another road, and a soil container disposed outside of said intersection, said soil bed being accommodated in said soil container and having plants cultivated thereon, said air outlet comprising a surface of said soil bed.

2. An apparatus according to claim 1, wherein said road has a median strip closely to said intersection, said soil container being disposed on said median strip.

* * * * *